(12) United States Patent
Cooper et al.

(10) Patent No.: US 9,532,870 B2
(45) Date of Patent: Jan. 3, 2017

(54) PROSTHETIC VALVE FOR REPLACING A MITRAL VALVE

(71) Applicant: Edwards Lifesciences Corporation, Irvine, CA (US)

(72) Inventors: Alexander H. Cooper, Newport Beach, CA (US); Matthew A. Peterson, Newport Beach, CA (US); William C. Brunnett, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 14/730,639

(22) Filed: Jun. 4, 2015

(65) Prior Publication Data

US 2015/0351904 A1    Dec. 10, 2015

Related U.S. Application Data

(60) Provisional application No. 62/009,072, filed on Jun. 6, 2014.

(51) Int. Cl.
*A61F 2/24* (2006.01)
*A61F 2/95* (2013.01)

(52) U.S. Cl.
CPC ............ *A61F 2/2418* (2013.01); *A61F 2/2409* (2013.01); *A61F 2/2436* (2013.01);
(Continued)

(58) Field of Classification Search
CPC ........ A61F 2/24; A61F 2/2418; A61F 2/2409; A61F 2/2436; A61F 2/2475; A61F 2/2478
(Continued)

(56) References Cited

U.S. PATENT DOCUMENTS

| 3,409,013 A | 11/1968 | Berry |
| 3,472,230 A | 10/1969 | Fogarty |

(Continued)

FOREIGN PATENT DOCUMENTS

| DE | 2246526 A1 | 3/1973 |
| DE | 19532846 A1 | 3/1997 |

(Continued)

OTHER PUBLICATIONS

Int'l. Search Report for PCT/US2015/034413 mailed Sep. 11, 2015.
(Continued)

*Primary Examiner* — Alvin Stewart
(74) *Attorney, Agent, or Firm* — Klarquist Sparkman LLP

(57) ABSTRACT

Embodiments of a prosthetic heart valve comprise an annular main body, an atrial cap extending radially outwardly from the atrial end of the main body, and a plurality of ventricular anchors extending outwardly from the ventricular end of the main body. Each ventricular anchor can have a proximal end portion connected to the ventricular end, an intermediate portion extending away from the atrial end and then back toward the atrial so as to define a first bend, and a free distal end portion that extends from the intermediate portion. The distal end portion can comprise a first section, a second section, and a second bend between the first and second sections, the first section extending from the intermediate portion in a direction toward the atrial end and radially away from the main body.

24 Claims, 21 Drawing Sheets

(52) U.S. Cl.
CPC ............... A61F 2002/9534 (2013.01); A61F 2220/0008 (2013.01); A61F 2230/005 (2013.01); A61F 2230/0065 (2013.01); A61F 2230/0078 (2013.01)

(58) Field of Classification Search
USPC .............................. 623/1.24, 1.26, 2.14, 2.18
See application file for complete search history.

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson, IV et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,306,141 B1 | 10/2001 | Jervis |
| 6,312,465 B1 | 11/2001 | Griffin et al. |
| 6,350,277 B1 | 2/2002 | Kocur |
| 6,379,372 B1 | 4/2002 | Dehdashtian et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,527,979 B2 | 3/2003 | Constantz |
| 6,569,196 B1 | 5/2003 | Vesely et al. |
| 6,575,959 B1 | 6/2003 | Sarge et al. |
| 6,582,462 B1 | 6/2003 | Andersen et al. |
| 6,605,112 B1 | 8/2003 | Moll |
| 6,730,118 B2 | 5/2004 | Spenser et al. |
| 6,733,525 B2 | 5/2004 | Yang et al. |
| 6,790,229 B1 | 9/2004 | Berreklouw |
| 6,830,584 B1 | 12/2004 | Seguin |
| 6,893,460 B2 | 5/2005 | Spenser et al. |
| 6,908,481 B2 | 6/2005 | Cribier |
| 6,974,476 B2 | 12/2005 | McGuckin, Jr. et al. |
| 7,018,406 B2 | 3/2006 | Seguin et al. |
| 7,195,641 B2 * | 3/2007 | Palmaz ............... A61F 2/2418 623/1.26 |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |

(56) References Cited

U.S. PATENT DOCUMENTS

| | | | |
|---|---|---|---|
| 7,318,278 B2 | 1/2008 | Zhang et al. | |
| 7,374,571 B2 | 5/2008 | Pease et al. | |
| 7,381,210 B2 | 6/2008 | Zarbatany et al. | |
| 7,393,360 B2 | 7/2008 | Spenser et al. | |
| 7,429,269 B2 | 9/2008 | Schwammenthal et al. | |
| 7,442,204 B2 | 10/2008 | Schwammenthal et al. | |
| 7,462,191 B2 | 12/2008 | Spenser et al. | |
| 7,510,575 B2 | 3/2009 | Spenser et al. | |
| 7,524,330 B2 | 4/2009 | Berreklouw | |
| 7,530,253 B2 | 5/2009 | Spenser et al. | |
| 7,579,381 B2 | 8/2009 | Dove | |
| 7,585,321 B2 | 9/2009 | Cribier | |
| 7,618,446 B2 | 11/2009 | Andersen et al. | |
| 7,621,948 B2 | 11/2009 | Herrmann et al. | |
| 7,704,222 B2 | 4/2010 | Wilk et al. | |
| 7,736,327 B2 | 6/2010 | Wilk et al. | |
| 7,892,281 B2 | 2/2011 | Seguin et al. | |
| 7,914,575 B2 | 3/2011 | Guyenot et al. | |
| 7,993,394 B2 | 8/2011 | Hariton et al. | |
| 8,007,992 B2 | 8/2011 | Tian et al. | |
| 8,029,556 B2 | 10/2011 | Rowe | |
| 8,092,520 B2 * | 1/2012 | Quadri | A61F 2/2418 623/1.26 |
| 8,092,521 B2 | 1/2012 | Figulla et al. | |
| 8,105,375 B2 * | 1/2012 | Navia | A61F 2/2418 623/2.1 |
| 8,118,866 B2 | 2/2012 | Herrmann et al. | |
| 8,167,932 B2 | 5/2012 | Bourang | |
| 8,167,934 B2 * | 5/2012 | Styrc | A61F 2/2418 623/2.1 |
| 8,206,437 B2 | 6/2012 | Bonhoeffer et al. | |
| 8,216,174 B2 | 7/2012 | Wilk et al. | |
| 8,317,858 B2 | 11/2012 | Straubinger et al. | |
| 8,398,704 B2 | 3/2013 | Straubinger et al. | |
| 8,416,643 B2 | 4/2013 | Magee | |
| 8,444,689 B2 * | 5/2013 | Zhang | A61F 2/2418 623/2.1 |
| 8,449,599 B2 * | 5/2013 | Chau | A61F 2/2418 623/1.24 |
| 8,460,370 B2 | 6/2013 | Zakay | |
| 8,540,768 B2 * | 9/2013 | Stacchino | A61F 2/2418 623/2.1 |
| 8,579,964 B2 * | 11/2013 | Lane | A61F 2/2418 623/2.11 |
| 8,685,086 B2 * | 4/2014 | Navia | A61F 2/2418 623/2.14 |
| 8,728,155 B2 * | 5/2014 | Montorfano | A61F 2/2409 623/2.18 |
| 8,795,356 B2 * | 8/2014 | Quadri | A61F 2/2418 623/2.11 |
| 8,828,078 B2 * | 9/2014 | Salahieh | A61F 2/2418 623/1.26 |
| 8,894,702 B2 * | 11/2014 | Quadri | A61F 2/2412 623/1.24 |
| 8,926,691 B2 * | 1/2015 | Chau | A61F 2/2418 606/108 |
| 9,023,100 B2 * | 5/2015 | Quadri | A61F 2/2418 623/2.11 |
| 9,034,032 B2 * | 5/2015 | McLean | A61F 2/2412 623/2.12 |
| 9,050,188 B2 * | 6/2015 | Schweich, Jr. | A61F 2/2409 |
| 9,125,740 B2 * | 9/2015 | Morriss | A61F 2/2418 |
| 9,186,249 B2 * | 11/2015 | Rolando | A61F 2/2418 |
| 9,232,995 B2 * | 1/2016 | Kovalsky | A61F 2/2412 |
| 2001/0021872 A1 * | 9/2001 | Bailey | A61F 2/2418 623/1.24 |
| 2002/0032481 A1 | 3/2002 | Gabbay | |
| 2002/0173842 A1 | 11/2002 | Buchanan | |
| 2003/0023300 A1 * | 1/2003 | Bailey | A61F 2/2418 623/1.13 |
| 2003/0050694 A1 | 3/2003 | Yang et al. | |
| 2003/0100939 A1 | 5/2003 | Yodfat et al. | |
| 2003/0158597 A1 | 8/2003 | Quiachon et al. | |
| 2003/0212454 A1 | 11/2003 | Scott et al. | |
| 2004/0039436 A1 | 2/2004 | Spenser et al. | |
| 2004/0092858 A1 | 5/2004 | Wilson et al. | |
| 2004/0133263 A1 | 7/2004 | Dusbabek et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0137688 A1 | 6/2005 | Salahieh et al. | |
| 2005/0137695 A1 * | 6/2005 | Salahieh | A61F 2/2418 623/2.11 |
| 2005/0137698 A1 | 6/2005 | Salahieh et al. | |
| 2005/0203614 A1 | 9/2005 | Forster et al. | |
| 2005/0234546 A1 | 10/2005 | Nugent et al. | |
| 2005/0288766 A1 | 12/2005 | Plain et al. | |
| 2006/0025857 A1 | 2/2006 | Bergheim et al. | |
| 2006/0058872 A1 | 3/2006 | Salahieh et al. | |
| 2006/0142837 A1 | 6/2006 | Haverkost et al. | |
| 2006/0149350 A1 | 7/2006 | Patel et al. | |
| 2006/0149360 A1 * | 7/2006 | Schwammenthal | A61F 2/2418 623/1.24 |
| 2006/0161249 A1 | 7/2006 | Realyvasquez et al. | |
| 2006/0195134 A1 | 8/2006 | Crittenden | |
| 2006/0195183 A1 * | 8/2006 | Navia | A61F 2/2409 623/2.18 |
| 2006/0229719 A1 | 10/2006 | Marquez et al. | |
| 2006/0241745 A1 | 10/2006 | Solem | |
| 2006/0259135 A1 | 11/2006 | Navia et al. | |
| 2006/0259137 A1 | 11/2006 | Artof et al. | |
| 2006/0276874 A1 | 12/2006 | Wilson et al. | |
| 2007/0005131 A1 | 1/2007 | Taylor | |
| 2007/0010877 A1 | 1/2007 | Salahieh et al. | |
| 2007/0027534 A1 | 2/2007 | Bergheim et al. | |
| 2007/0043435 A1 * | 2/2007 | Seguin | A61F 2/2418 623/2.11 |
| 2007/0066863 A1 | 3/2007 | Rafiee et al. | |
| 2007/0088431 A1 | 4/2007 | Bourang et al. | |
| 2007/0100439 A1 | 5/2007 | Cangialosi et al. | |
| 2007/0112422 A1 | 5/2007 | Dehdashtian | |
| 2007/0142906 A1 | 6/2007 | Figulla et al. | |
| 2007/0156224 A1 | 7/2007 | Cioanta et al. | |
| 2007/0203503 A1 | 8/2007 | Salahieh et al. | |
| 2007/0203575 A1 | 8/2007 | Forster et al. | |
| 2007/0213813 A1 | 9/2007 | Von Segesser et al. | |
| 2007/0270943 A1 | 11/2007 | Solem | |
| 2007/0288087 A1 * | 12/2007 | Fearnot | A61F 2/2418 623/1.24 |
| 2008/0065011 A1 | 3/2008 | Marchand et al. | |
| 2008/0071361 A1 | 3/2008 | Tuval et al. | |
| 2008/0071362 A1 | 3/2008 | Tuval et al. | |
| 2008/0071363 A1 | 3/2008 | Tuval et al. | |
| 2008/0071366 A1 | 3/2008 | Tuval et al. | |
| 2008/0071368 A1 | 3/2008 | Tuval et al. | |
| 2008/0071369 A1 | 3/2008 | Tuval et al. | |
| 2008/0082166 A1 | 4/2008 | Styrc et al. | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0161911 A1 | 7/2008 | Revuelta et al. | |
| 2008/0208323 A1 | 8/2008 | Antocci et al. | |
| 2008/0208332 A1 | 8/2008 | Lamphere et al. | |
| 2008/0221672 A1 | 9/2008 | Lamphere et al. | |
| 2008/0255660 A1 | 10/2008 | Guyenot et al. | |
| 2008/0255661 A1 | 10/2008 | Straubinger et al. | |
| 2008/0281411 A1 | 11/2008 | Berreklouw | |
| 2009/0005863 A1 * | 1/2009 | Goetz | A61F 2/2418 623/2.18 |
| 2009/0054968 A1 | 2/2009 | Bonhoeffer et al. | |
| 2009/0054974 A1 | 2/2009 | McGuckin, Jr. et al. | |
| 2009/0062901 A1 * | 3/2009 | McGuckin, Jr. | A61F 2/2418 623/1.15 |
| 2009/0076598 A1 | 3/2009 | Salahieh et al. | |
| 2009/0112309 A1 * | 4/2009 | Jaramillo | A61F 2/2412 623/1.26 |
| 2009/0138079 A1 | 5/2009 | Tuval et al. | |
| 2009/0157175 A1 | 6/2009 | Benichou | |
| 2009/0164005 A1 | 6/2009 | Dove et al. | |
| 2009/0171432 A1 | 7/2009 | Von Segesser et al. | |
| 2009/0171447 A1 | 7/2009 | Von Segesser et al. | |

(56) References Cited

U.S. PATENT DOCUMENTS

| | | |
|---|---|---|
| 2009/0171456 A1 | 7/2009 | Kveen et al. |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1* | 9/2009 | Tuval ............... A61F 2/2418 623/1.24 |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0319037 A1 | 12/2009 | Rowe et al. |
| 2010/0016958 A1 | 1/2010 | St. Goar et al. |
| 2010/0049313 A1 | 2/2010 | Alon et al. |
| 2010/0131054 A1 | 5/2010 | Tuval et al. |
| 2010/0137979 A1 | 6/2010 | Tuval et al. |
| 2010/0174362 A1 | 7/2010 | Straubinger et al. |
| 2010/0204781 A1 | 8/2010 | Alkhatib |
| 2010/0217382 A1 | 8/2010 | Chau et al. |
| 2010/0256723 A1* | 10/2010 | Murray ............... A61F 2/2418 623/1.2 |
| 2010/0262231 A1 | 10/2010 | Tuval et al. |
| 2011/0015616 A1 | 1/2011 | Straubinger et al. |
| 2011/0015729 A1 | 1/2011 | Jimenez et al. |
| 2011/0022157 A1* | 1/2011 | Essinger ............... A61F 2/2418 623/1.26 |
| 2011/0137397 A1 | 6/2011 | Chau et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0238159 A1 | 9/2011 | Guyenot et al. |
| 2011/0288634 A1 | 11/2011 | Tuval et al. |
| 2011/0319989 A1 | 12/2011 | Lane et al. |
| 2012/0035722 A1 | 2/2012 | Tuval |
| 2012/0046741 A1 | 2/2012 | Tuval et al. |
| 2012/0046742 A1 | 2/2012 | Tuval et al. |
| 2012/0078353 A1* | 3/2012 | Quadri ............... A61F 2/2418 623/2.11 |
| 2012/0101570 A1 | 4/2012 | Tuval et al. |
| 2012/0123529 A1 | 5/2012 | Levi et al. |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0271398 A1* | 10/2012 | Essinger ............... A61F 2/2412 623/1.11 |
| 2012/0283823 A1 | 11/2012 | Bonhoeffer et al. |
| 2012/0296418 A1 | 11/2012 | Bonyuet et al. |
| 2012/0310336 A1 | 12/2012 | Figulla et al. |
| 2013/0073035 A1 | 3/2013 | Tuval et al. |
| 2013/0079869 A1 | 3/2013 | Straubinger et al. |
| 2013/0144380 A1 | 6/2013 | Quadri et al. |
| 2013/0190862 A1 | 7/2013 | Pintor et al. |
| 2013/0197622 A1 | 8/2013 | Mitra et al. |
| 2013/0261739 A1* | 10/2013 | Kuehn ............... A61F 2/2412 623/2.11 |
| 2013/0304200 A1* | 11/2013 | McLean ............... A61F 2/2436 623/2.18 |
| 2013/0310928 A1* | 11/2013 | Morriss ............... A61F 2/2418 623/2.12 |
| 2014/0046434 A1* | 2/2014 | Rolando ............... A61F 2/2418 623/2.11 |
| 2014/0052237 A1* | 2/2014 | Lane ............... A61F 2/2412 623/2.11 |
| 2014/0142694 A1* | 5/2014 | Tabor ............... A61F 2/013 623/2.18 |
| 2014/0214159 A1* | 7/2014 | Vidlund ............... A61L 27/34 623/2.14 |
| 2014/0277390 A1* | 9/2014 | Ratz ............... A61F 2/2418 623/1.26 |
| 2015/0297381 A1* | 10/2015 | Essinger ............... A61F 2/2412 623/1.12 |
| 2016/0022444 A1* | 1/2016 | Delaloye ............... A61F 2/95 623/1.11 |
| 2016/0030171 A1* | 2/2016 | Quijano ............... A61F 2/243 623/1.12 |
| 2016/0051362 A1* | 2/2016 | Cooper ............... A61F 2/2403 623/2.18 |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 102006052564 B3 | 12/2007 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1469797 A1 | 10/2004 |
| EP | 1570809 A1 | 9/2005 |
| EP | 1653888 A2 | 5/2006 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 91/17720 A1 | 11/1991 |
| WO | 92/17118 A1 | 10/1992 |
| WO | 9301768 A1 | 2/1993 |
| WO | 97/24080 A1 | 7/1997 |
| WO | 98/29057 A1 | 7/1998 |
| WO | 99/33414 A1 | 7/1999 |
| WO | 99/40964 A1 | 8/1999 |
| WO | 99/47075 A1 | 9/1999 |
| WO | 00/18333 A1 | 4/2000 |
| WO | 00/41652 A1 | 7/2000 |
| WO | 00/47139 A1 | 8/2000 |
| WO | 0128459 A1 | 4/2001 |
| WO | 01/35878 A2 | 5/2001 |
| WO | 01/49213 A2 | 7/2001 |
| WO | 01/62189 A1 | 8/2001 |
| WO | 0154624 A1 | 8/2001 |
| WO | 0154625 A1 | 8/2001 |
| WO | 01/64137 A1 | 9/2001 |
| WO | 01/76510 A2 | 10/2001 |
| WO | 02/22054 A1 | 3/2002 |
| WO | 02/36048 A1 | 5/2002 |
| WO | 02/41789 A2 | 5/2002 |
| WO | 02/43620 A1 | 6/2002 |
| WO | 02/47575 A2 | 6/2002 |
| WO | 02/49540 A2 | 6/2002 |
| WO | 03/047468 A1 | 6/2003 |
| WO | 2005/034812 | 4/2005 |
| WO | 2005/087140 A1 | 9/2005 |
| WO | 2005/102015 | 11/2005 |
| WO | 2006/014233 A2 | 2/2006 |
| WO | 2006/034008 A2 | 3/2006 |
| WO | 2006/108090 | 10/2006 |
| WO | 2006/111391 | 10/2006 |
| WO | 2006/138173 | 12/2006 |
| WO | 2008/005405 A2 | 1/2008 |
| WO | 2008/035337 A2 | 3/2008 |
| WO | 2008/147964 A1 | 3/2008 |
| WO | 2008/150529 A1 | 12/2008 |
| WO | 2009/024859 | 2/2009 |
| WO | 2009/116041 | 9/2009 |

OTHER PUBLICATIONS

Al-Khaja, N., et al., "Eleven Years' Experience with Carpentier-Edwards Biological Valves in Relation to Survival and Complica-

(56) References Cited

OTHER PUBLICATIONS tions," European Journal of Cardiothoracic Surgery 3:305-311, Jun. 30, 2009.

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Al Zaibag, Muayed, et al., "Percutaneous Balloon Valvotomy in Tricuspid Stenosis," British Heart Journal, Jan. 1987, vol. 57, No. 1, pp. 51-53.

Andersen, et al., "Transluminal implantation of artificial heart valves. Description of a new expandable aortic valve and initial results with implantation by catheter technique in closed chest pigs." European Heart Journal (1992), 13, 704-708.

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Dake, Transluminal Placement of Endovascular Stent-Grafts for the Treatment of Descending Thoracic Aortic Aneurysms, New Engl. J.Med., 1994; 331:1729 34.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Kolata, Gina, "Device That Opens Clogged Arteries Gets a Failing Grade in a New Study," nytimes.com, http://www.nytimes.com/1991/01/03/health/device-that-opens-clogged-arteries-gets-a-faili . . . , Jul. 29, 2009, 2 pages.

Inoue, M.D., Kanji, et al., "Clinical Application of Transvenous Mitral Commissurotomy by a New Balloon Catheter," The Journal of Thoracic and Cardiovascular Surgery 87:394-402, 1984.

Lawrence, Jr., M.D., David D., "Percutaneous Endovascular Graft: Experimental Evaluation," Radiology 1897; 163: 357-360.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann, W., et al., "Der Verschluβ des Ductus Arteriosus Persistens ohne Thorakotomie," Thoraxchirurgie Vaskuläre Chirurgie, Band 15, Heft 2, Stuttgart, im Apr. 1967, pp. 199-203.

Rashkind, M.D., William J., "Creation of an Atrial Septal Defect Withoput Thoracotomy," the Journal of the American Medical Association, vol. 196, No. 11, Jun. 13, 1966, pp. 173-174.

Rashkind, M.D., William J., "Historical Aspects of Interventional Cardiology: Past, Present, Future," Texas Heart Institute Journal, Interventional Cardiology, pp. 363-367.

Rösch, M.D., Josef, "The Birth, Early Years and Future of Interventional Radiology," J Vasc Interv Radiol 2003; 14:841-853.

Ross, F.R.C.S., D.N., "Aortic Valve Surgery," Guys Hospital, London, pp. 192-197, approximately 1968.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Selby, M.D., J. Bayne, "Experience with New Retrieval Forceps for Foreign Body Removal in the Vascular, Urinary, and Biliary Systems," Radiology 1990; 176:535-538.

Serruys, P.W., et al., "Stenting of Coronary Arteries. Are we the Sorcerer's Apprentice?," European Heart Journal (1989) 10, 774-782, pp. 37-45, Jun. 13, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida, Barry T., et al., "Modifications of Gianturco Expandable Wire Stents," AJR:150, May 1988, Dec. 3, 1987, pp. 1185-1187.

Urban, M.D., Philip, "Coronary Artery Stenting," Editions Médecine et Hygiène, Geneve, 1991, pp. 5-47.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

Wheatley, M.D., David J., "Valve Prostheses," Rob & Smith's Operative Surgery, Fourth Edition, pp. 415-424, Butterworths 1986.

* cited by examiner

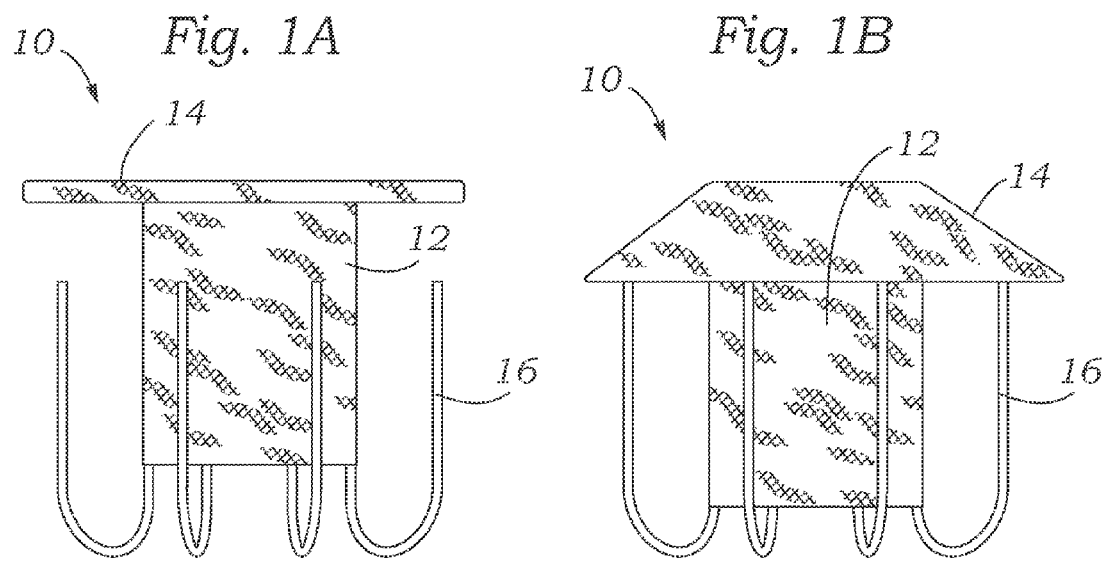
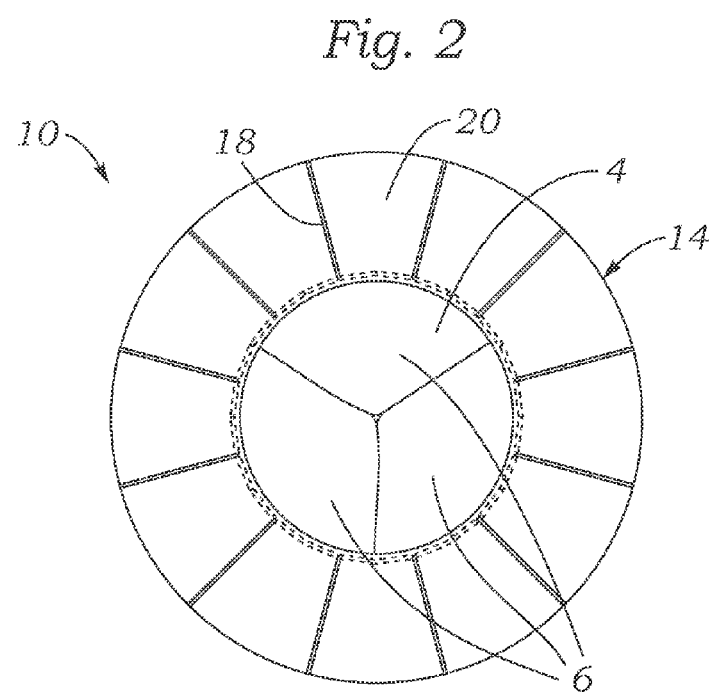

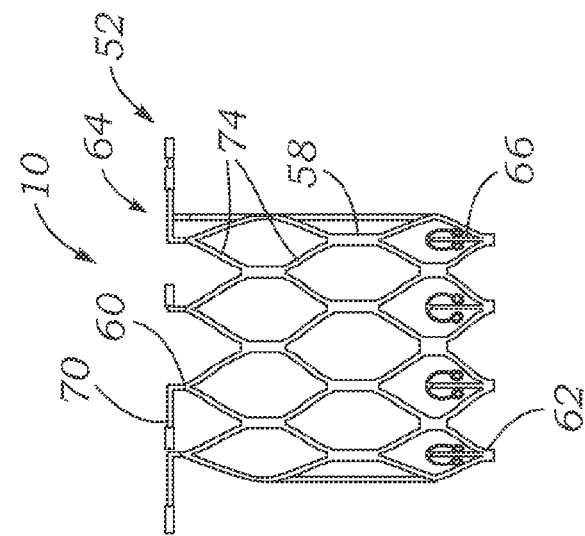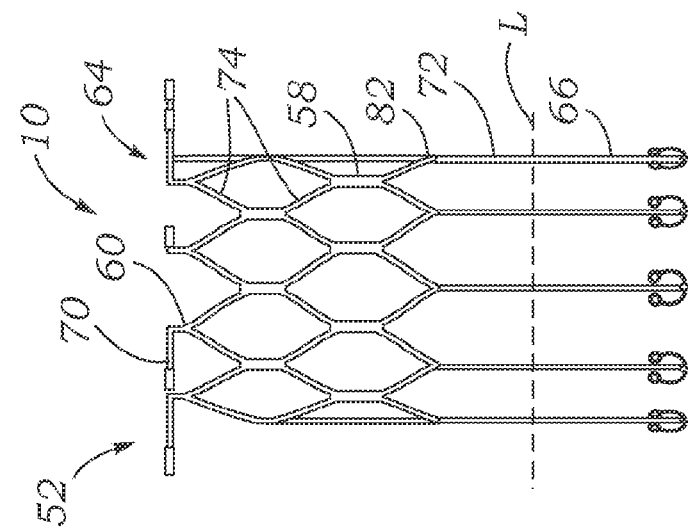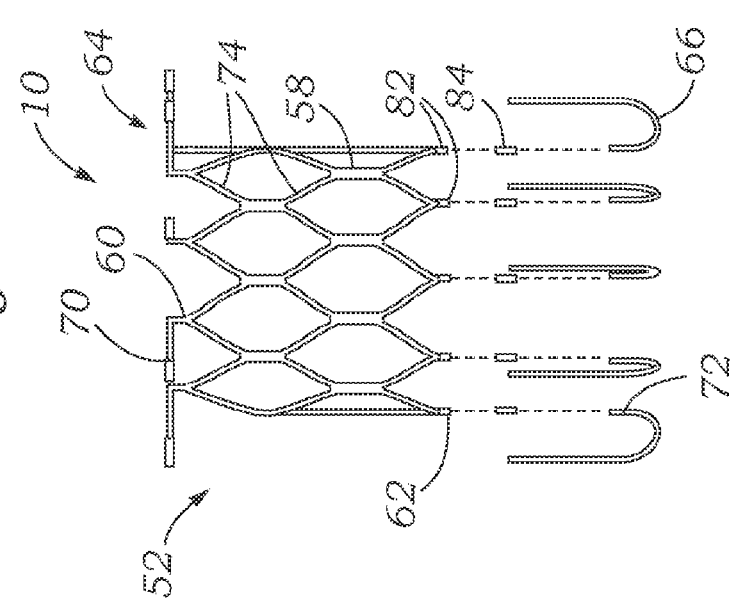

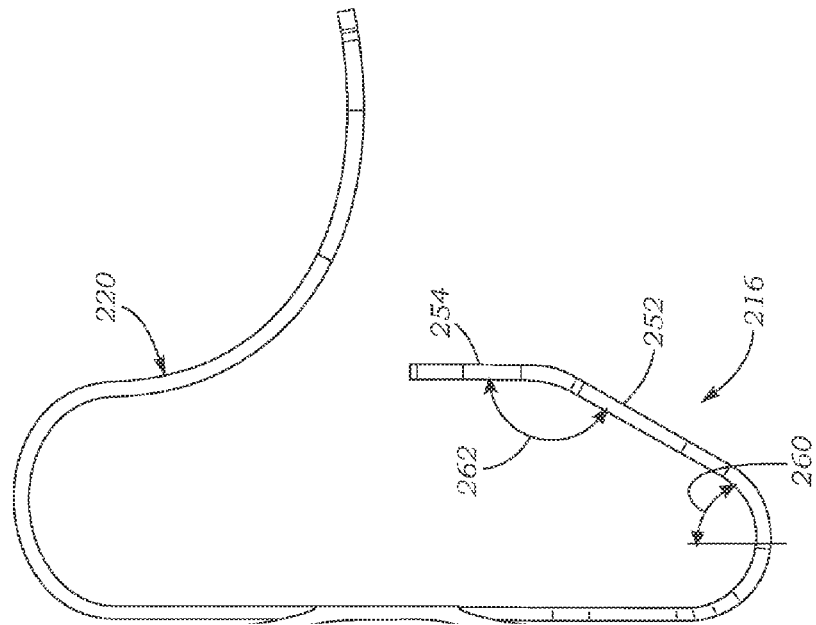
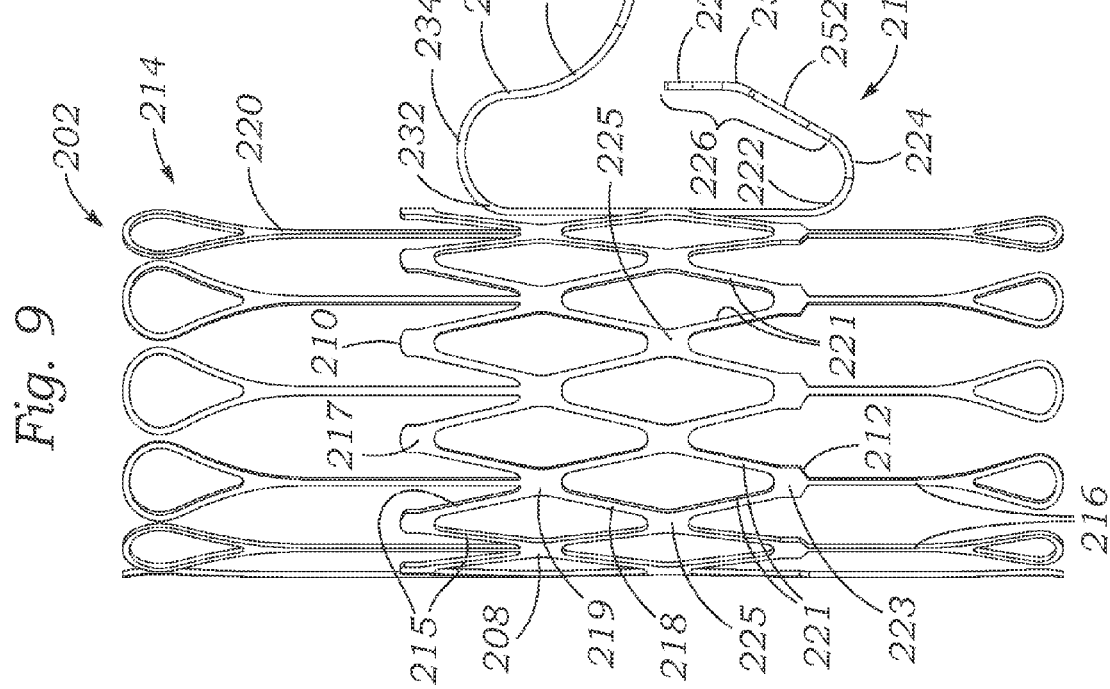

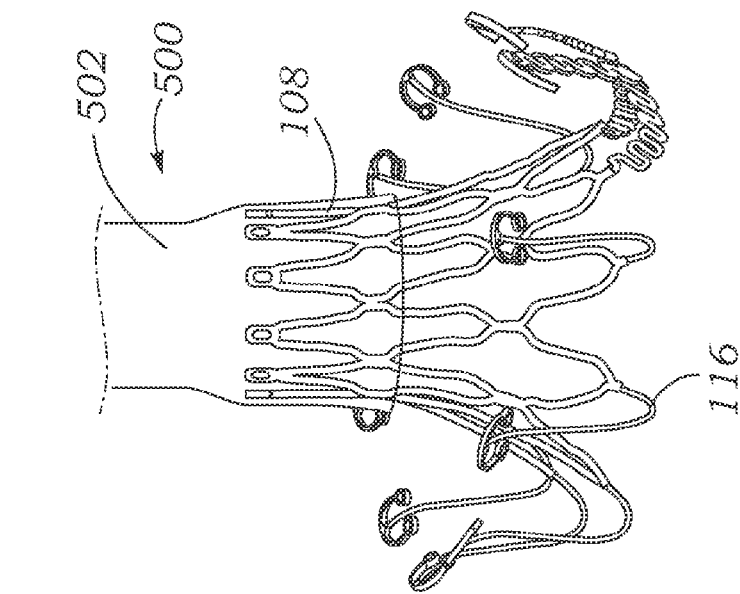
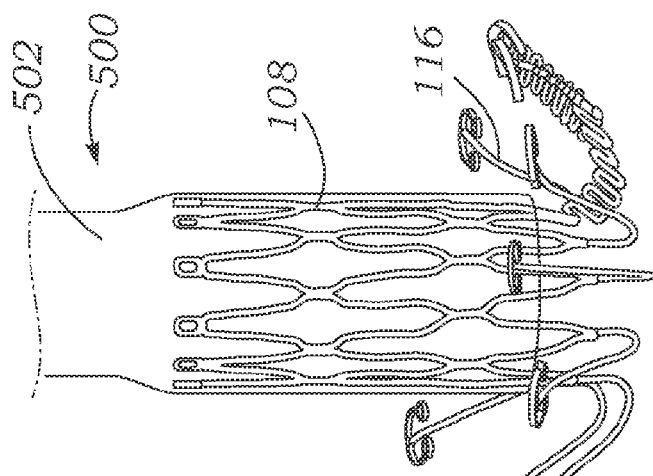
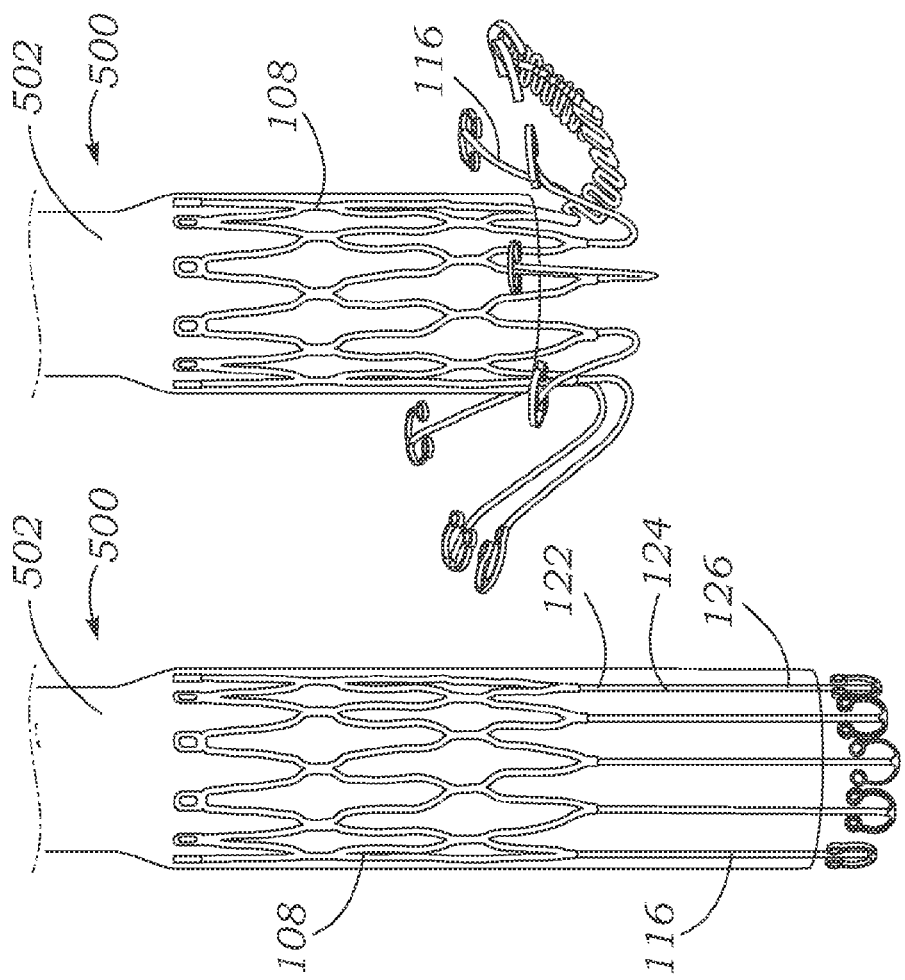

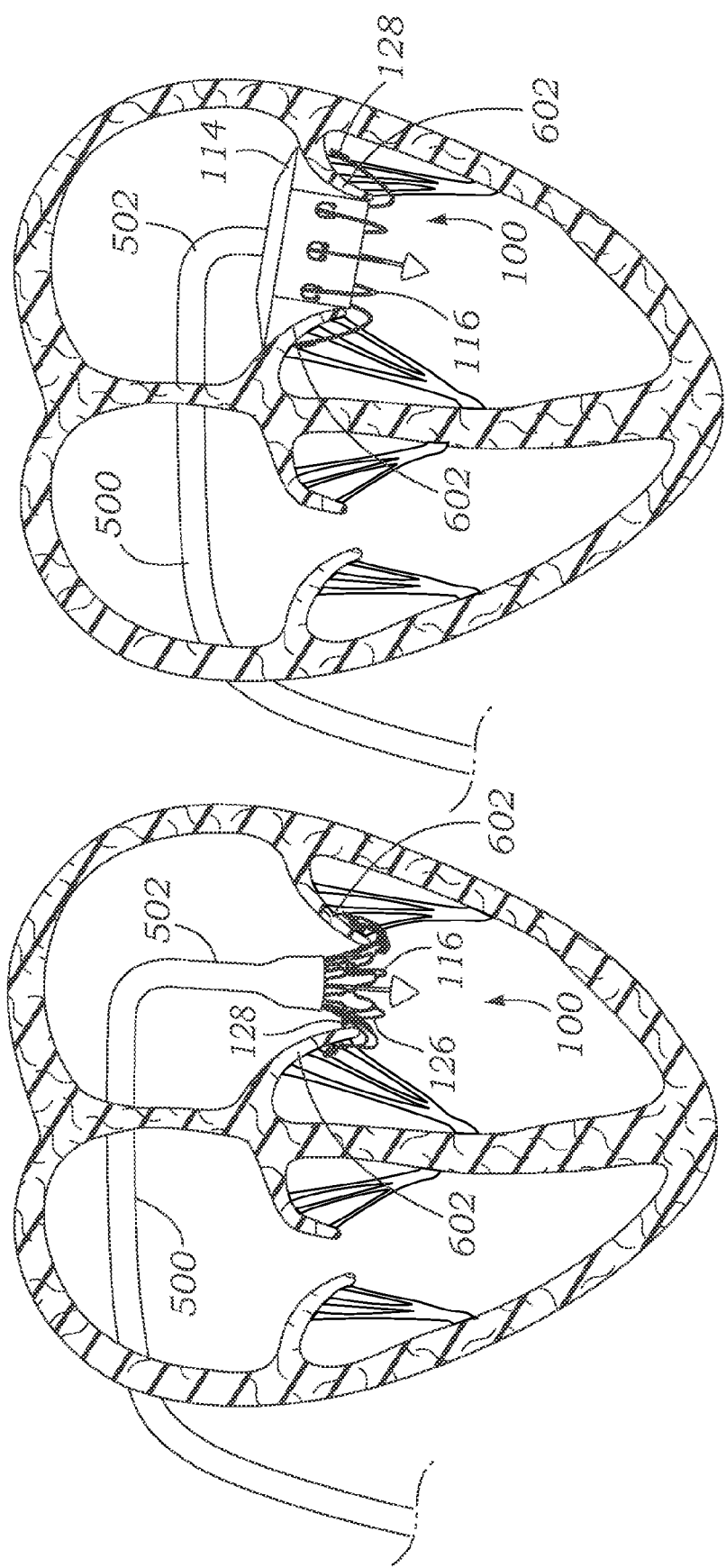

PROSTHETIC VALVE FOR REPLACING A MITRAL VALVE

CROSS-REFERENCE TO RELATED APPLICATION

The present application claims the benefit of U.S. Provisional Application No. 62/009,072, filed Jun. 6, 2014, which is incorporated herein by reference.

FIELD

This disclosure pertains generally to prosthetic devices for repairing and/or replacing native heart valves, and in particular to prosthetic valves for replacing defective mitral valves, as well as methods and devices for delivering and implanting the same within a human heart.

BACKGROUND

Prosthetic valves have been used for many years to treat cardiac valvular disorders. The native heart valves (i.e., the aortic, pulmonary, tricuspid, and mitral valves) serve critical functions in assuring the forward flow of an adequate supply of blood through the cardiovascular system. These heart valves can be rendered less effective by congenital malformations, inflammatory processes, infectious conditions, or disease. Such damage to the valves can result in serious cardiovascular compromise or death. For many years the definitive treatment for such disorders was the surgical repair or replacement of the valve during open-heart surgery. Such surgeries are highly invasive and are prone to many complications, however. Therefore, elderly and frail patients with defective heart valves often go untreated. More recently a transvascular technique has been developed for introducing and implanting a prosthetic heart valve using a flexible catheter in a manner that is much less invasive than open-heart surgery.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve, such as by inflating a balloon on which the prosthetic valve is mounted.

Another known technique for implanting a prosthetic aortic valve is a transapical approach where a small incision is made in the chest wall of a patient and the catheter is advanced through the apex (i.e., bottom tip) of the heart. Like the transvascular approach, the transapical approach can include a balloon catheter having a steering mechanism for delivering a balloon-expandable prosthetic heart valve through an introducer to the aortic annulus. The balloon catheter can include a deflectable segment just proximal to the distal balloon to facilitate positioning of the prosthetic heart valve in the proper orientation within the aortic annulus.

The above techniques and others have provided numerous options for high operative risk patients with aortic valve disease to avoid the consequences of open heart surgery and cardiopulmonary bypass. While devices and procedures for the aortic valve are well-developed, such catheter-based procedures are not necessarily applicable to the mitral valve due to the distinct differences between the aortic and mitral valve. The mitral valve has a complex subvalvular apparatus, e.g., the chordae tendineae and papillary muscles, which is not present in the aortic valve.

Surgical mitral valve repair techniques (e.g., mitral annuloplasty) have increased in popularity due to their high success rates, and clinical improvements after repair. In addition to existing mitral valve repair technologies, there are a number of new technologies aimed at making mitral valve repair a less invasive procedure. These technologies range from iterations of the Alfieri stitch procedure, to coronary-sinus-based modifications of mitral anatomy, to subvalvular plications or ventricular remodeling devices, which would incidentally correct mitral regurgitation.

However, for mitral valve replacement, few less-invasive options are available. There are approximately 25,000 mitral valve replacements (MVR) each year in the United States. However, it is estimated that over 300,000 patients meeting the guidelines for treatment are denied treatment based on their ages and/or co-morbidities. Thus, a need exists for minimally invasive techniques for replacing the mitral valve.

In particular, a need exists for minimally invasive techniques with enhanced ease of implantation and reduced risk of misplacement due to operator error or biological variability. Specifically, a need exists for prosthetic heart valves that can be deployed within the valve annulus and that do not require a particular angular alignment. A need also exists for prosthetic heart valves that can move synchronously with the native valve annulus.

SUMMARY

In one representative embodiment, a prosthetic device is provided for implanting at a native mitral or tricuspid valve region of the heart, the native valve region having a native valve annulus and native leaflets. The prosthetic device can comprise a main body configured for placement within the native mitral valve annulus, the main body having a lumen extending between an atrial end and a ventricular end. The prosthetic device can also have an atrial cap extending radially outwardly from the atrial end of the main body. The prosthetic device can also have a plurality of ventricular anchors spaced angularly around a circumference of the main body. Each ventricular anchor can have a proximal end portion connected to the main body at locations proximate the ventricular end, an intermediate portion extending away from the atrial end and then back toward the atrial end so as to define a first bend, and a free distal end portion that extends from the intermediate portion, the distal end portion comprising a first section, a second section, and a second bend between the first and second sections, the first section extending from the intermediate portion in a direction toward the atrial end and radially away from the main body.

In some embodiments, at least one of the ventricular anchors of the prosthetic device comprises a pattern of repeating turns (such as a serpentine pattern).

In some embodiments, the atrial cap comprises a plurality of angularly spaced atrial anchors, each having a proximal end portion connected to the atrial end of the main body and a distal end portion extending generally downwardly toward the ventricular end.

In some embodiments, the proximal end portions of the atrial anchors project upward into the atrium and curved intermediate portions of the atrial anchors connect the proximal end portions to the distal end portions.

In some embodiments, the atrial cap blocks blood from flowing beyond the atrial end of the main body, along the outside of the main body, when the prosthetic device is implanted.

In some embodiments, the main body is radially compressible to a radially compressed state for delivery into the heart and can self-expand from the compressed state to a radially expanded state.

In some embodiments, in a radially compressed state, each ventricular anchor is linearly extended, such that the proximal end portions and distal end portions are axially aligned, parallel to the axis of the main body.

In some embodiments, the plurality of ventricular anchors is connected to the main body independently of each other without frame segments interconnecting adjacent ventricular anchors.

In some embodiments, the free end portions of the ventricular anchors each comprise a curved or rounded element.

In some embodiments, the plurality of atrial anchors is connected to the main body independently of each other without frame segments interconnecting adjacent atrial anchors.

In some embodiments, the first sections of the distal end portions of the ventricular anchors extend away from a longitudinal axis of the main body and the second sections of the distal end portions extend substantially parallel to the longitudinal axis.

In some embodiments, the second sections of the distal end portions curve toward the atrial end and back toward the ventricular end of the main body.

In some embodiments, the atrial anchors have varying lengths and/or the ventricular anchors have varying lengths.

In some embodiments, the ventricular anchors can be connected to the ventricular end of the main body.

In some embodiments, the ventricular anchors can be connected to the main body at locations spaced from the ventricular end of the main body.

In another representative embodiment, a prosthetic device can have a main body and an atrial cap extending radially outward from the atrial end of the main body. When released from a delivery sheath, the atrial cap can transform from a radially compressed, cylindrical shape extending from the atrial end of the main body to a deployed state in which the atrial cap extends radially outward and curls below the atrial end toward the ventricular end of the main body.

In some embodiments, the prosthetic device can have a plurality of ventricular anchors extending from the ventricular end of the main body.

In some embodiments, the main body can have a cylindrical inlet portion defining an inlet diameter of the main body and a tapered outlet portion defining an outlet diameter of the main body, wherein the outlet diameter is smaller than the inlet diameter.

In some embodiments, the ventricular anchors can have curved portions that extend away from the ventricular end of the main body and curve back toward the atrial end of the main body, wherein the curved portions have a reduced thickness relative to the remaining portions of the anchors.

In another representative embodiment, a method is provided for implanting a prosthetic heart valve at a native atrioventricular valve region having a native valve annulus and a plurality of native leaflets. The method can comprise providing a transcatheter prosthetic heart valve contained within an interior of a sheath of a delivery apparatus, wherein the prosthetic heart valve comprises an annular main body and a plurality of ventricular anchors extending from the main body, the ventricular anchors being connected to the main body independently of each other without frame segments interconnecting adjacent anchors. The method can further comprise delivering the prosthetic device to the native valve region and deploying the prosthetic heart valve from the sheath such that the main body expands within the native annulus and the plurality of ventricular anchors extend behind the native leaflets. Each ventricular anchor has a proximal end portion extending in a direction away from the atrial end of the main body, an intermediate portion extending back toward the atrial end, and a distal end portion extending toward the atrial end and radially away from the main body.

In some embodiments, the native valve annulus is the mitral valve annulus and the prosthetic heart valve is delivered to the annulus via the left atrium.

In some embodiments, a distal end portion of one or more of the plurality of ventricular anchors projects upward to contact a ventricular surface of the native valve annulus.

In some embodiments, the method further comprises wrapping one or more of the ventricular anchors behind the native leaflets.

In some embodiments, delivering the prosthetic valve comprises transporting the prosthetic heart valve across the atrial septum into the left atrium.

In some embodiments, deployment of the main body causes the distal end portions of the ventricular anchors to rotate toward the main body.

In some embodiments, following deployment, the prosthetic valve and the native valve annulus move in a generally synchronous manner during cardiac cycling.

In some embodiments, the method further comprises advancing the outer sheath distally to recapture the plurality of ventricular anchors within the interior of the outer sheath.

BRIEF DESCRIPTION OF THE FIGURES

FIG. 1A is a side schematic view of an exemplary prosthetic valve, according to one embodiment.

FIG. 1B is a side schematic view of another exemplary prosthetic valve.

FIG. 2 is a top schematic view of the prosthetic valve of FIG. 1A or FIG. 1B.

FIGS. 3A-3C are side schematic views of three bare frames for use in a prosthetic valve, which illustrate three exemplary methods for manufacturing and shaping a frame according to the present disclosure.

FIG. 6A shows a ventricular anchor having a pattern of coils. FIG. 6B shows a ventricular anchor having a serpentine pattern. FIG. 6C shows a ventricular anchor having a helical pattern.

FIG. 9 is a side view of another exemplary frame for use in a prosthetic valve, with a single atrial anchor and a corresponding ventricular anchor shown in a deployed configuration for purposes of illustration. The remaining atrial and ventricular anchors are shown in a non-deployed, delivery configuration. FIG. 9A is an enlarged view of the atrial anchor and the ventricular anchor that are shown in the deployed configuration in FIG. 9.

FIGS. 15A-15C show an exemplary method for deploying a prosthetic valve from a retractable sheath.

FIGS. 16A-16D show an exemplary method for implanting a prosthetic valve at the mitral valve annulus region via a transseptal approach.

DETAILED DESCRIPTION

Overview

Figure 4:
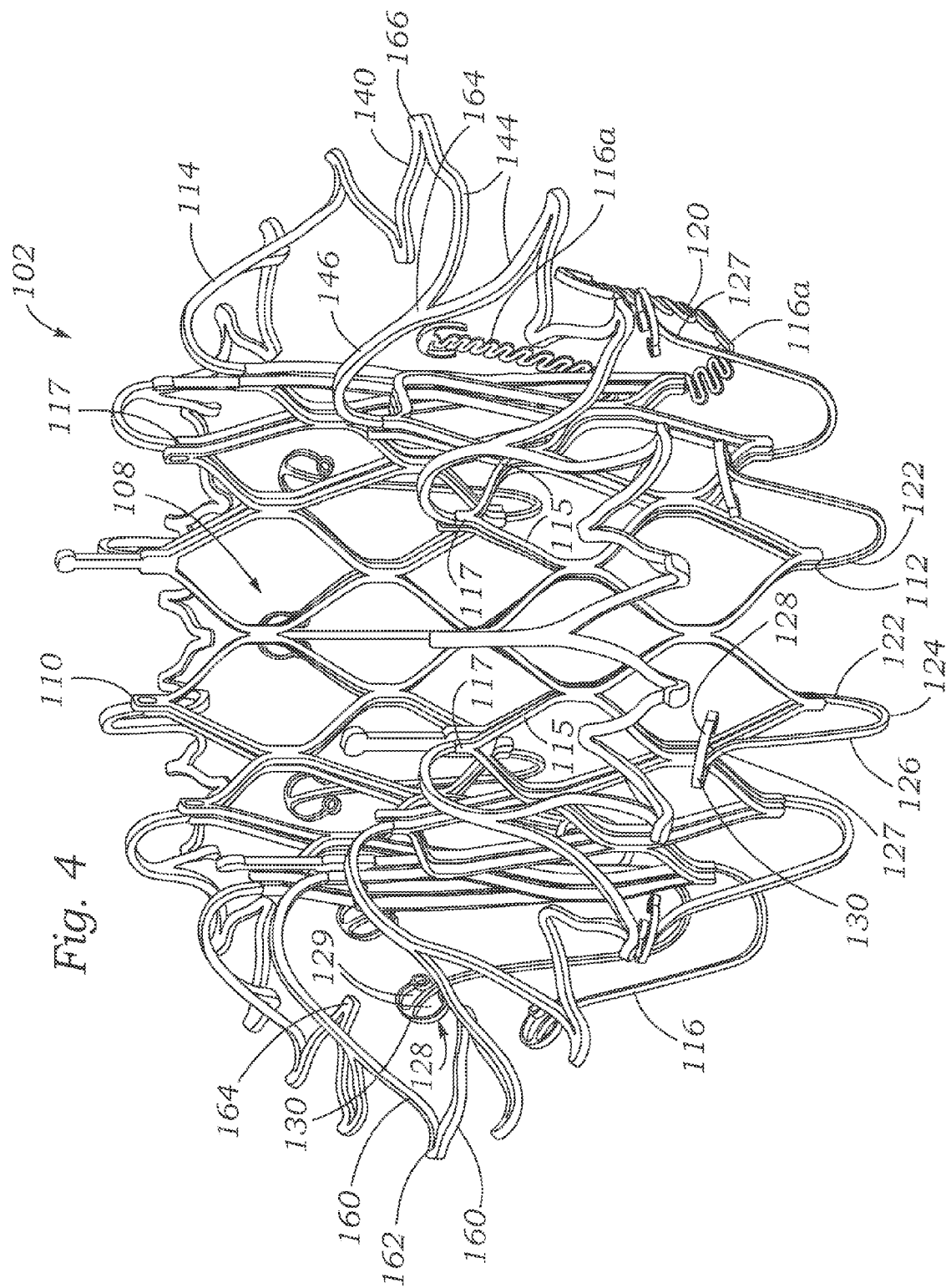
FIG. 4 is a top-sided perspective view of an exemplary frame for use in a prosthetic valve.

When a native valve fails to function properly, a prosthetic valve replacement can help restore the proper functionality. Compared to the aortic valve, however, which has a relatively round and firm annulus (especially in the case of aortic stenosis), the mitral valve annulus can be relatively less firm and more unstable. Consequently, it may not be possible to secure a prosthetic valve that is designed primarily for the aortic valve within the native mitral valve annulus by relying solely on friction from the radial force of an outer surface of a prosthetic valve pressed against the native mitral annulus.

Described herein are embodiments of prosthetic valves and components thereof that are primarily intended to be implanted at the mitral valve region of a human heart, as well as devices and methods for implanting the same. The prosthetic valves can be used to help restore and/or replace the functionality of a defective native valve. These prosthetic valves are not restricted to use at the native mitral valve annulus, however, and can be used to replace other valves within the heart, such as the tricuspid valve, aortic valve, and pulmonary valve. In some cases, the disclosed devices can also be used to replace a venous valve or generate a valved or valveless fistula or patent foramen ovale (PFO).

In general, the prosthetic valves described herein employ an "atrial cap" and ventricular anchors instead of (or in addition to) radial friction forces, to secure the prosthetic valve within the native valve annulus. The atrial cap can comprise a plurality of atrial anchors spaced angularly around a circumference of the prosthetic valve. The atrial anchors can together form an atrial sealing portion that extends radially outward and downward, from the main body, to cover the atrial surface of the native annulus.

FIGS. 1A, 1B and 2 illustrate the general concept for the prosthetic valve, showing two exemplary prosthetic valve embodiments 10. FIG. 1A is a side view of a first embodiment of the prosthetic valve. FIG. 1B is a side view of a second embodiment of the prosthetic valve. FIG. 2 is a top plan view applicable to both embodiments. Each prosthetic valve 10 has a valve structure 4 comprising a plurality of leaflets 6, and a frame comprising a main body (which is covered by an outer skirt 12), an atrial cap member 14 extending from the inflow end of the main body, and a plurality of ventricular anchors 16 extending from the outflow end of the main body. The atrial cap 14 can be configured to apply a constant pressure on the atrial surface of the native valve annulus. As shown in FIG. 1B, the atrial cap 14 can be angled downwardly toward the ventricular anchors to produce or to augment this pressure. In other embodiments, as shown in FIG. 1A, the cap 14 is substantially flat and extends radially outwardly at about a 90-degree angle relative to the main body.

The atrial cap 14 can further comprise a plurality of radially-extending support elements, arms, struts, or anchors 18 (FIG. 2). The support elements 18 and/or the spaces in between the elements 18 can be covered by a blood-impermeable material cover or layer 20 (e.g., a biocompatible fabric or tissue material layer). In this manner, the atrial cap 14 can block blood from flowing back into the left atrium between the outer surfaces of the prosthetic valve 100 and the native valve tissue during systole. The atrial cap can also ensure that all, or substantially all, of the blood passes through the one-way valve as it flows from the left atrium to the left ventricle during diastole. As such, the atrial cap prevents or reduces perivalvular leakage.

The skirt 12 can be connected to the inner and/or outer surfaces of the main body to form at least one layer or envelope covering some or all of the openings in the main body. The skirt 12 can be connected to the frame, for example, by sutures. The skirt 12 and the layer 20 can comprise a fabric that is impermeable to blood but can allow for tissue ingrowth. The skirt 12 and the layer 20 can comprise synthetic materials, such as polyester material or a biocompatible polymer. One example of a polyester material is polyethylene terephthalate (PET). Another example is expanded polytetrafluoroethylene (ePTFE), either alone, or in combination at least one other material. Alternative materials can also be used. For example, the skirt 12 and the layer 20 can comprise biological matter, such as pericardial tissue (e.g., bovine, porcine, or equine pericardium) or other biological tissue.

In some embodiments, the atrial cap 14 can comprise a plurality of atrial arms or anchors, which can project radially outward and/or downward to provide an effective, atraumatic sealing configuration, as further described below. These atrial anchors and/or the spaces between the anchors can be covered by a blood-impermeable material.

As discussed above, in the embodiment illustrated in FIG. 1B, the atrial cap 14 is angled or concave downwards. The atrial cap comprises atrial anchors 18 (FIG. 2) that angle downwards from an inlet end of a frame 58 (FIGS. 3A-3C), forming acute angles therewith. Some embodiments of an angled atrial cap 14 generate a downward force on the native valve annulus, improving a compressive seal with the native valve annulus. Moreover, in some embodiments in which at least one atrial anchor 18 or one group of atrial anchors is independently movable or positionable with respect to another, the atrial anchors 18 better conform to the shape of the native valve. For example, the native mitral valve complex, including the annulus, trigones, and leaflets, typically has a saddle shape on the atrial side. Such atrial anchors 18 also permit the atrial cap 14 to accommodate movement of the heart tissue over the cardiac cycle. This adaptability to the shape and/or movement of the native tissue improves sealing and/or reduces perivalvular leakage in some embodiments.

The ventricular anchors 16 can be configured to extend into the ventricle and to project back upward towards the native valve annulus. The ventricular anchors 16 can be spaced angularly around a circumference of a ventricular end of the prosthetic valve 10. In the illustrated embodiment, the ventricular anchors are connected to the main body of the frame independently of each other, that is, without additional metal frame segments or struts interconnecting adjacent anchors. In this manner, each ventricular anchor can flex relative to the others, as well as relative to the main body to ensure or facilitate the anchors closely engaging adjacent tissue in the left ventricle, including the native leaflets, the trigone areas, and/or the chordae tendineae. The anchors 16 can be configured such that their distal ends contact a ventricular side of the native valve annulus and/or an adjacent tissue region (such as one or more trigone areas). Proximal end portions of the anchors 16 can extend downward from the main body into the ventricle, intermediate portions of the anchors can wrap behind the leaflets, and distal end portions can extend upward to (optionally) contact the native annulus and/or adjacent tissue areas. One or more of the ventricular anchors 16 can, but need not necessarily, pin or otherwise capture a leaflet between the anchor and the main body.

In some embodiments, the individual atrial and/or ventricular anchors have equal lengths and/or are substantially symmetrically arranged around the main body. In other embodiments, at least one atrial and/or ventricular anchor independently has a different length and/or is asymmetrically arranged around the respective end of the main body compared with one or more other anchors of the same type. In some cases, the native valve annulus is asymmetrical in shape, such that having atrial and/or ventricular anchors with non-equal lengths and/or asymmetrical arrangements is desirable. In some cases, shorter atrial and/or ventricular anchors can be placed adjacent to thinner areas of the atrial or ventricular septum. Additionally, the aortic valve is positioned behind the anterior leaflet of the native mitral valve, so the atrial anchors and/or ventricular anchors facing anteriorly (i.e., facing the aortic valve) may be relatively shorter to avoid disrupting or otherwise interfering with the function of the aortic valve. Finally, some embodiments comprise longer ventricular anchors that project upward to contact the native valve annulus and shorter ventricular anchors that do not project as far upward. In some embodiments, one or more of the shorter ventricular anchors projects upward to interact with the chordae tendineae.

In some embodiments, the individual atrial and/or ventricular anchors have a consistent thickness along their respective lengths. In other embodiments, one or more of the individual atrial and/or ventricular anchors have a variable thickness along its length. Varying the thickness of anchor can provide benefits with regard to strain reduction, for example, helping to reduce plastic deformation and risk of fracture. A variable thickness can also make the anchors flexible at certain points to help reduce the stress placed on adjacent anatomical structures.

When used to refer to portions of a ventricular or atrial anchor, the terms "proximal" and "distal" refer to locations relative to the attachment point of the anchor to the main body of the frame. The "proximal end" of the anchor is the end closest to the attachment point of the anchor to the main body. The "distal end" of the anchor is the end farthest away from the attachment point of the anchor to the main body when the anchor is fully extended.

The plurality of ventricular anchors 16 can be spaced around the circumference of the prosthetic valve at about equal intervals. In other embodiments, the spacing between ventricular anchors is not equal. In some embodiments, the ventricular anchors can extend radially outward and upward (toward the annulus), and thus, in certain embodiments, the distance between distal end portions of adjacent ventricular anchors is greater than the distance between proximal end portions of the ventricular anchors. In various embodiments, the contact between the ventricular anchors (which may be covered with a layer of fabric or tissue) and tissue in the vicinity of the native valve annulus (along the ventricular side) can also promote tissue in-growth.

By "sandwiching" the native valve annulus from the atrial and ventricular sides, the prosthetic valve 10 can move with the native annulus in a generally synchronous manner. Synchronous movement of an implanted prosthetic valve 10 can confer specific advantages, including faster and/or improved endothelialization, enhanced in-growth, reduced abrasion of surrounding tissue, and enhanced durability of the prosthetic device. Furthermore, in addition to providing an anchoring means for the prosthetic valve 10, the ventricular anchors 16 can remodel the left ventricle to help treat an underlying cause of mitral regurgitation: left ventricle enlargement/dilation. The ventricular anchors 16 can pull the native mitral valve leaflets closer together and toward the left atrium and, via the chordae tendineae, thereby pull the papillary muscles closer together, which can positively remodel the ventricle acutely and prevent the left ventricle from further enlarging. Thus, the ventricular anchors 16 can also be referred to as tensioning members or reshaping members.

As used herein, the terms "downward" and "upward" are merely terms of convenience. A prosthetic device for implantation in a mitral valve annulus, for example, will be positioned such that a ventricular anchor configured to project back toward the atrium and native valve annulus will thereby be substantially extending "upward." Likewise, an atrial anchor or other rim portion configured to project in the direction of the ventricle will thereby be extending "downward." In general, because the use of the terms "upward" and "downward" are merely conventions, there is no absolute requirement for the ventricular anchor to be oriented substantially or even partially "downward" (relative to the user, subject or environment) when the device is in use. Except for when indicated, the positions and orientations of frame components (such as ventricular anchors) are described in the expanded configuration.

Additional Frame and Prosthetic Valve Embodiments

FIGS. 3A-3C show three exemplary frame configurations 52 that can be used for the prosthetic valve 10, including manufacturing details and assembly techniques. The frame 52 can comprise a main body 58, an atrial cap 64 and plurality of ventricular anchors 66. The main body 58 can comprise three (or more) rows of circumferentially-extending, angled struts 74. The atrial cap 64 can be substantially flat and can comprise a plurality of arms 70 projecting radially outward from points along the main body 58, spaced circumferentially apart around an atrial end 60 of the main body.

As shown in FIG. 3A, the ventricular anchors 66 can be manufactured as separate pieces, and subsequently connected together at a plurality of connection locations 82 spaced circumferentially apart around a ventricular end 62 of the main body 58. To assemble the frame, a proximal end portion 72 of each ventricular anchor 66 can be brought into the vicinity of a connection location 82, and a sleeve 84 (such as a crimp sleeve) can be passed over both the connection location 82 and the proximal end portion 72. The sleeve 84 can then be compressed (e.g., crimped) to securely join the proximal end portion 72 to the connection location 82. In addition to or in lieu of the sleeve 84, the anchors 66 can be welded to the frame 52 at the connection points 82.

Alternatively, as shown in FIGS. 3B-3C, the frame 52, the atrial arms 70, and the plurality of ventricular anchors 66 can be manufactured as a single unitary structure, such as by laser cutting the frame from a metal tube. The ventricular anchors 66 can then be shape set, such as through the use of heat, to produce the requisite conformational properties, including having an upward bias.

As shown in FIG. 3B, in some embodiments, the anchors 66 can be manufactured such that they extend axially away from the main body. A "fold line" L is shown extending through the proximal end portions 72 of the anchors 66, which guides shape setting. From this fold line, the anchors 66 can be biased to turn upward toward the frame 52 (as shown in FIGS. 1A and 1B).

In alternative embodiments, as shown in FIG. 3C, the frame 52 can have an extra row of struts 74 (compared to the embodiments shown in FIGS. 3A-3B), with the anchors 66 projecting radially outwardly from the bottom row of struts and toward the atrial end of the main body.

Figure 5:
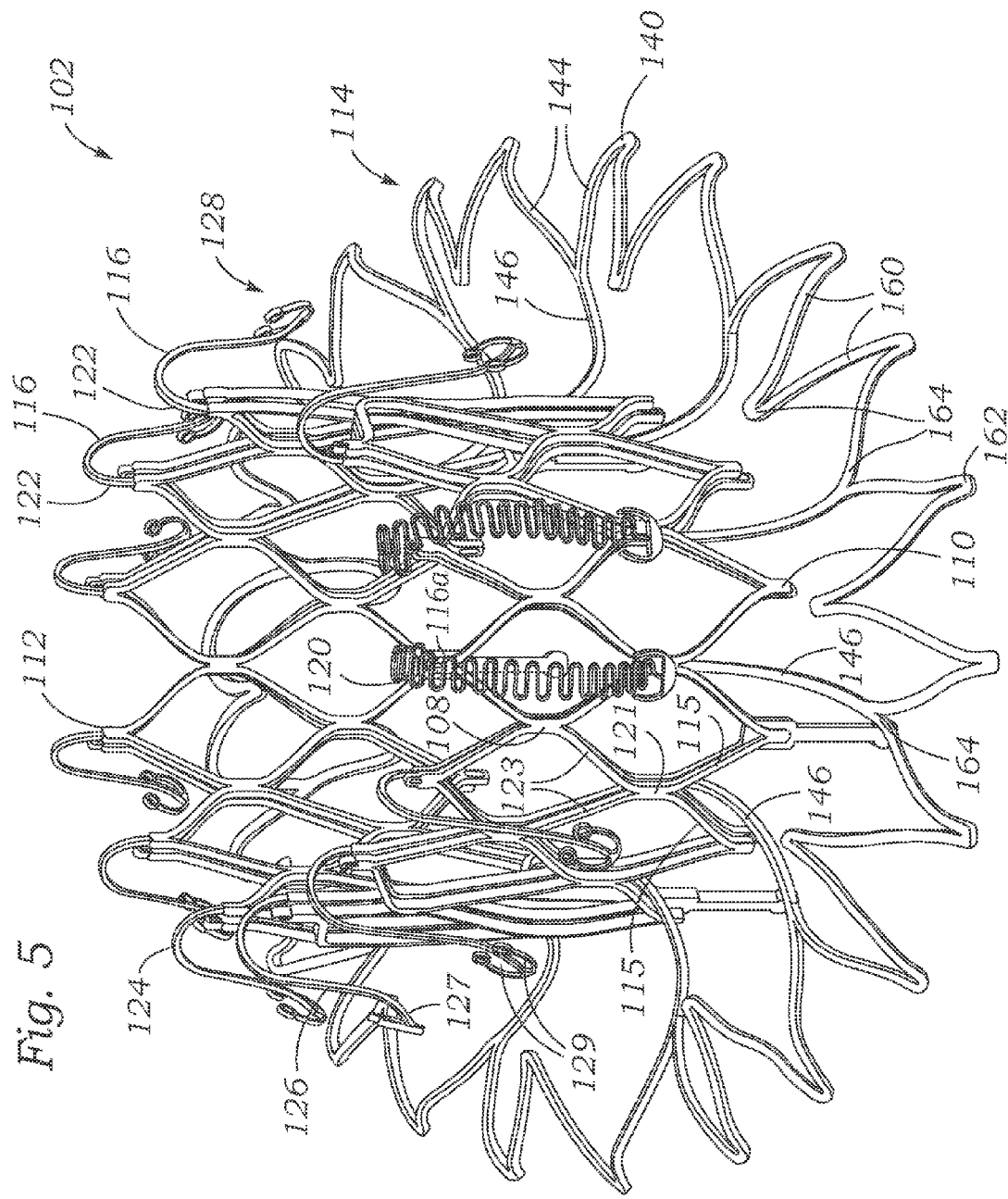
FIG. 5 is a bottom-sided perspective view of another exemplary frame for use in a prosthetic valve.

FIGS. 4-5 illustrate two exemplary bare frames 102 (in an expanded configuration) for use in a prosthetic valve. The frame 102 can comprise a tubular or annular main body 108, an atrial cap 114 extending radially outwardly from an atrial end 110 of the main body 108, and a plurality of ventricular anchors 116 extending from a ventricular end 112 of the main body 108. When the frame 102 is implanted in the native mitral valve region of the heart, the main body 108 can be positioned within the native mitral valve annulus with the ventricular end 112 of the main body 108 being a lower, outlet end, the atrial end 110 of the main body 108 being an upper, inlet end, the ventricular anchors 116 being located in the left ventricle, and the atrial cap 114 being located in the left atrium. The embodiments of FIGS. 4 and 5 are similar except for the particular locations at which the atrial cap 114 connects to the main body, as further described below.

The prosthetic valve can comprise a valve structure supported by and/or within the frame 102. The valve structure can include a plurality of prosthetic leaflets and/or other components for regulating the flow of blood in one direction through the prosthetic valve. For example, valve structure can be oriented within the frame 102 such that an upper end of the valve structure is the inflow end and a lower end of the valve structure is the outflow end. The leaflets can comprise any of various suitable materials, such as natural tissue (e.g., bovine pericardial tissue) or synthetic materials. The valve structure can be mounted to the frame 102 using suitable techniques and mechanisms. In some embodiments, leaflets can be sutured to the frame 102 in a tricuspid arrangement. The prosthetic valve can also include a blood-impermeable skirt mounted on the outside and/or the inside of the main body.

Additional details regarding components and assembly of prosthetic valves (including techniques for mounting leaflets to the frame) are described, for example, in U.S. Patent Application Publication No. 2009/0276040 A1 and U.S. Patent Publication No. 2010/0217382 A1, which are incorporated by reference herein.

In an expanded state, as shown in FIGS. 4-5, the main body 108 of the frame 102 can form an open-ended tube. An outer surface of the main body 108 can have dimensions similar to that of the mitral orifice, i.e., the inner surface of the mitral annulus, but not necessarily. In some embodiments, for example, the outer surface of the main body 108 can have diametrical dimensions that are smaller than the diametrical dimensions of the native mitral orifice, such that the main body 108 can fit within the mitral orifice in the expanded state without substantially stretching the native mitral annulus. In such embodiments, the frame 102 need not rely on a pressure fit, or friction fit, between the outer surface of the main body 108 and the inner surface of the mitral annulus for prosthetic valve retention. Instead, the frame 102 can rely on the ventricular anchors 116 and/or the atrial cap 114 for retention. In other embodiments, however, the main body 108 can be configured to expand to an equal or greater size than the native mitral orifice and thereby create a pressure fit when implanted, which can be complementary to the use of ventricular anchors and/or the atrial cap for retention.

The frame 102 can have a wire mesh configuration and can be radially collapsible and expandable between a radially expanded state and a radially compressed state to enable delivery and implantation at an atrioventricular valve region of the heart (i.e., at the mitral or tricuspid valve region). The wire mesh can include metal wires or struts arranged in a lattice pattern, such as a sawtooth or zig-zag pattern, but other patterns may also be used. The frame 102 can comprise a shape-memory material, such as nitinol, to enable self-expansion from the radially compressed state to the expanded state. In other embodiments, the frame 102 can be plastically expandable from a radially compressed state to an expanded state by an expansion device, such as an inflatable balloon (not shown), for example. Such plastically expanding frames can comprise stainless steel, chromium alloys, and/or other suitable materials.

In the illustrated embodiment, the frame 102 comprises a total of twelve ventricular anchors 116. In other embodiments, the frame can have a fewer or greater number of ventricular anchors, however. The ventricular anchors 116 can each further comprise a proximal or fixed end portion 122, an intermediate portion 124 and a distal or free end portion 126. The proximal end portion 122 can be connected directly to the ventricular end 112 of the main body 108, and can project downwardly (into the ventricle toward the apex). The intermediate portion 124, located between the proximal end portion 122 and the distal end portion 126, can be curved such that the intermediate portion 124 extends downwardly from the proximal end portion 122 and then changes direction to extend upwardly toward the mitral valve annulus. The curved intermediate portion 124 can form between about a quarter-turn and about a half-turn, such that the curved segment forms an atraumatic surface for contacting adjacent tissue and structures, such as the chordae tendineae. In some embodiments, the anchors 116 also extend radially outward relative to the main body 108, and thereby project in an angled direction.

The distal end portion 126 can finally terminate in a curved, atraumatic head portion 128 having a distal end surface 130 for contacting the native valve annulus. Each distal head portion 128 can comprise a pair of open areas 129 through which tissue can protrude (e.g., tissue on the ventricular side of the native valve annulus tissue). Some embodiments of the head portion have a different shape, for example, a closed shape, a circle, an oval shape, a teardrop shape, a cupped shape, a coil, a spiral, or a serpentine shape. Some embodiments of the frame 102 comprise at least one first distal portion with a different shape from at least one second distal head portion. In some embodiments, the head portion 128 is angled relative to the remainder of the distal end portion 126. For example, as shown in FIGS. 4-5, the head portions 128 can be configured to splay radially outward relative to the rest of the distal end portions 126. Thus, the angle of the head portion 128, relative to the longitudinal axis of the main body 108, can be greater than the angle of the remainder of the distal end portion 126. As shown, the distal end portion 126 comprises an upper section 127 (proximal to the head portion 128) which splays radially outward, relative to the remainder of the distal end portion 126. In some embodiments, the upper section 127 is curved. In some embodiments, the head portion 128 splays radially outward, while the upper section 127 does not splay radially outward.

Figure 6A:
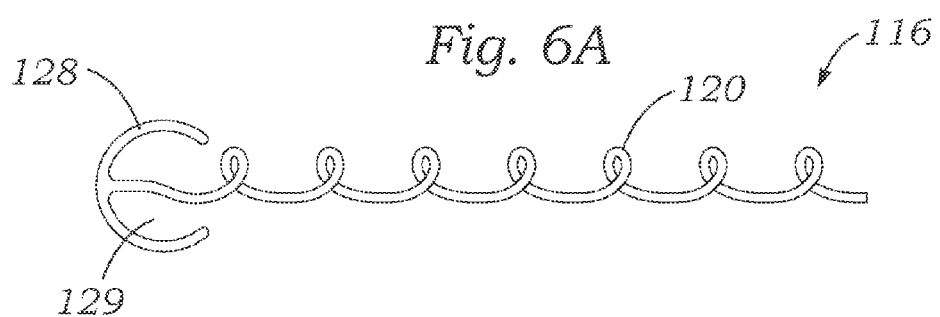
FIGS. 6A-6C show three exemplary ventricular anchors for use in a prosthetic valve, each featuring a repeating pattern of turns.
Figure 6B:
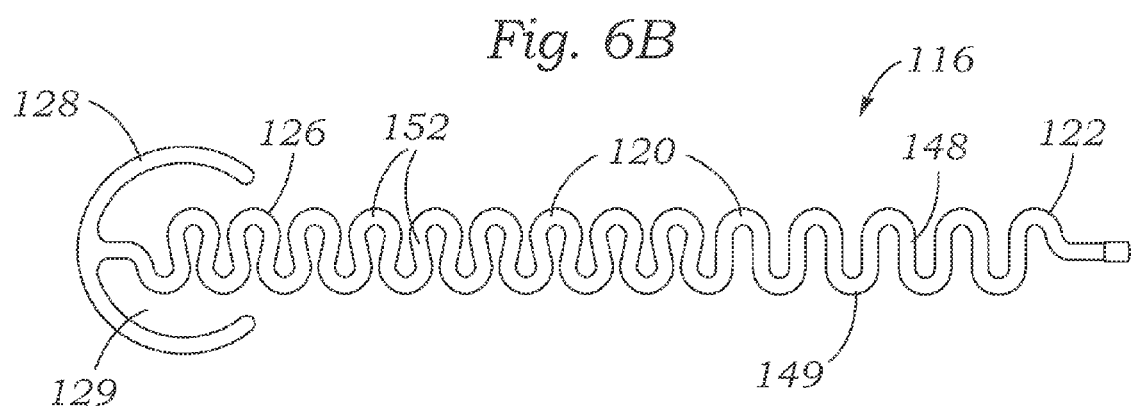
Figure 6C:
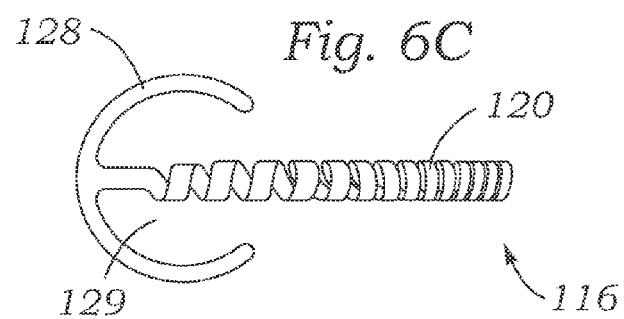

One or more of the ventricular anchors 116 can be substantially flexible (and/or more flexible than the other anchors 116) and may include a pattern of repeating turns 120. FIGS. 4-5 show two such flexible ventricular anchors 116a positioned adjacent to one another. Other embodiments include a greater or fewer number of flexible ventricular anchors 116a. For example, some embodiments include no flexible ventricular anchors, while in other embodiments all of the ventricular anchors are flexible ventricular anchors. A "turn" as used herein can refer to any curved portion which forms a generally circular path and/or encompasses a complete change in direction. FIGS. 6A-6C show different configurations for a ventricular anchor 116 comprising a pattern of repeating turns.

A turn can encompass, for example, a two-dimensional looped coil configuration (FIG. 6A), a three-dimensional helical configuration (FIG. 6C), or a serpentine configuration (FIGS. 4-5 and 6B). "Serpentine," as used herein, refers to a configuration in which a series of numerous segments are connected by curved intermediate portions to form a generally linear overall arrangement. In some cases, at least one of the anchors has a serpentine configuration comprising a plurality of substantially straight, parallel segments. In some cases, at least one of the anchors has a serpentine configuration comprising a plurality of substantially curved segments. In some cases, as shown in FIG. 6B, at least one of the anchors has a serpentine segment comprising both a plurality of substantially straight, parallel segments and a plurality of substantially curved segments. In other embodiments, a flexible ventricular anchor 116a comprises a different pattern, for example, a zigzag or sinusoidal pattern. Some embodiments of the flexible ventricular anchor comprises a combination of at least one more flexible portion, for example, a portion comprising a pattern of repeating turns, and at least one less flexible portion, for example, a substantially straight portion. Some embodiments comprise a combination of flexible portions, for example, a serpentine portion and a helical portion.

In various embodiments, the more flexible ventricular anchors 116a can be positioned adjacent to sensitive anatomical structures, such as adjacent the ventricular septum in the vicinity of the native mitral valve annulus. In various embodiments, the more flexible (e.g., serpentine) anchors can have the same overall shape as the less flexible ventricular anchors, to various extents. For example, while they can be shaped or otherwise biased to curve upward like the other anchors, it may not be necessary to specifically shape them to splay radially outward, given their flexibility. The possible variations for the ventricular anchors 116, for example, length and radial extent, also apply to the flexible ventricular anchors.

As shown in FIG. 6B, ventricular anchors 116 having a serpentine shape can comprise a group of substantially straight, parallel segments 148 and/or a group of substantially curved segments 152. The segments 148 can be interconnected by curved connecting segments or bends 149. In some embodiments, the anchors 116 can have straighter portions nearer the main body 108 (i.e., the proximal end portions 122) and more curved portions nearer the terminal ends (i.e., the distal end portions 126). In some embodiments, the serpentine shape (such as the parallel segments and/or the curved bends) can be thicker at the proximal end portions 122 than at the distal end portions 126. Including a serpentine shape in the anchors 116 can decrease their stiffness and/or decrease the chance of they will fail due to fatigue. In some embodiments, by increasing the thickness of the serpentine anchors, their flexibility is decreased, and by decreasing their thickness, their flexibility is increased.

Referring again to FIGS. 4-5, the atrial cap 114 can be integral with the main body 108 and comprised of the same wire mesh lattice as the main body 108 such that the atrial cap 114 can also be radially collapsible and expandable. The atrial cap 114 can also be radially collapsible and expandable. The atrial cap 114 can be cut from the same tubing as the main body 108 of the frame 102. In other embodiments, the atrial cap is manufactured as a separate component and subsequently attached to the main body, for example, using any of the methods described above for attaching the ventricular anchors 116 to the main body. The atrial cap 114 desirably exhibits sufficient stiffness to prevent the main body 108 from embolizing into the ventricle, but enough flexibility to avoid or reduce trauma to the native valve anatomy.

In some embodiments, in the expanded state, the atrial cap 114 is generally frustoconical. In some embodiments, the atrial cap 114 has a cellular structure. In some embodiments, the contact between the atrial cap 114 and the tissue of the atrial walls and/or the atrial face of the native valve annulus can promote tissue in-growth with the frame, which can improve retention and reduce perivalvular leakage. The atrial cap 114 is desirably configured to provide a substantially effective seal immediately on implantation, and thus does not necessarily require tissue in-growth for effective sealing. Nonetheless, an atrial cap that requires tissue in-growth to provide an effective seal may be desirable in certain circumstances, and is encompassed within the scope of the present disclosure.

The atrial cap 114 can comprise an integrated structure with an outer rim 140 sized and shaped to contact the atrial side of the mitral annulus and tissue of the left atrium when the frame 102 is implanted. The end plan view profile of the outer rim 140 can have a generally circular, oval, or other shape (e.g., a D-shape) that generally corresponds to the native geometry of the atrial wall and the mitral annulus. The outer rim 140 can have a stellate profile comprising a pattern of outwardly protruding triangular rim portions 144 extending around a circumference of the frame 102 at the atrial end 110.

The rim portions 144 comprise a plurality of angled struts 160 connected to each other at radial outer junctions or nodes 162 and at radial inner junctions or nodes 164. The struts 160 can be connected to the main body by radially extending struts 146. As shown in FIGS. 4-5, the struts 146 can extend from every other junction 164 of adjacent triangular rim portions 144 to the atrial end 110 of the main body 108. In other embodiments, the struts 146 and junctions 164 have a different periodicity, for example, from 1:3, 1:4, a different ratio, or a combination of ratios. In some cases, as shown in FIG. 4, the struts 146 can be connected to the apices 117 of the angled struts 115 of the uppermost row of struts of the main body at the atrial end 110 of the main body. Alternatively, as shown in FIG. 5, the struts 146 can be connected to junctions or nodes 121 at which adjacent angled struts 115 from the uppermost row of struts intersect the ends of struts 123 in an adjacent row of struts. Some embodiments include at least one strut connected to an apex and at least one strut connected to a node.

In the embodiments illustrated in FIGS. 4 and 5, the body 108 of the frame 102 has a double-body structure, including an annular outer portion overlapping an annular inner portion. In the illustrated embodiments, the atrial cap 114 extends from the outer portion of the body 108, while the ventricular anchors 116 extend from the inner portion. In other embodiments, the configuration is reversed, with the atrial cap 114 associated with the outer portion and the ventricular anchors 116 with the inner portion; or with both the atrial cap 114 and the ventricular anchors 116 extending from the same portion; or with another combination. In the illustrated embodiments, the atrial cap 114 and the outer portion are integral; and the ventricular anchors 116 and the inner portion are integral. As discussed above, in some embodiments, at least some of the ventricular anchors and/or atrial cap portions are manufactured separately from the body 108 and later attached thereto.

In the illustrated embodiments, the inner and outer portions of the body 108 are coextensive and their struts structures mirror each other and completely overlap each other. In other embodiments, each of the struts of the inner and/or outer portion does not have a counterpart in the other portion. The inner and outer portions are attached to each other, for example, by welding, using interlocking tabs, using suture or wire, and/or with pins.

Embodiments of stent bodies 108 having double-body structures permit increased control over the stent properties, for example, a body with both stiffer and more flexible portions. In some embodiments, one of the inner portion and outer portion is thicker than the other, resulting in thicker ventricular anchors or a thicker atrial cap. Some embodiments are better able to withstand mechanical strain during delivery and/or the cardiac cycle.

FIGS. 7-10 show additional alternative prosthetic valve frame embodiments 202 which comprise a main body 208 (having an atrial end 210 and ventricular end 212), ventricular anchors 216, and an atrial cap 214 having a plurality of atrial anchors 220. The atrial anchors 220 and the ventricular anchors 216 can be spaced angularly apart around the circumference of the atrial end 210 and ventricular end 212, respectively. In some cases, the atrial anchors 220 and/or the ventricular anchors 216 are spaced apart at equal intervals. The atrial anchors 220 in the illustrated embodiment are connected to the main body 208 independently of each other, without additional frame segments or struts interconnecting adjacent atrial anchors 220, allowing the atrial anchors to flex relative to each other and the main body 208. For purposes of illustration, only one atrial anchor 220 and one ventricular anchor 216 are shown in the deployed configuration in FIGS. 9-10. Gaps 213 between adjacent atrial anchors 220 accommodate tissue, including the mitral valve annulus, the trigones, and the native mitral valve leaflets, as well as permitting the atrial anchors to independently adjust to and conform to each patient's particular anatomy.

Figure 7:
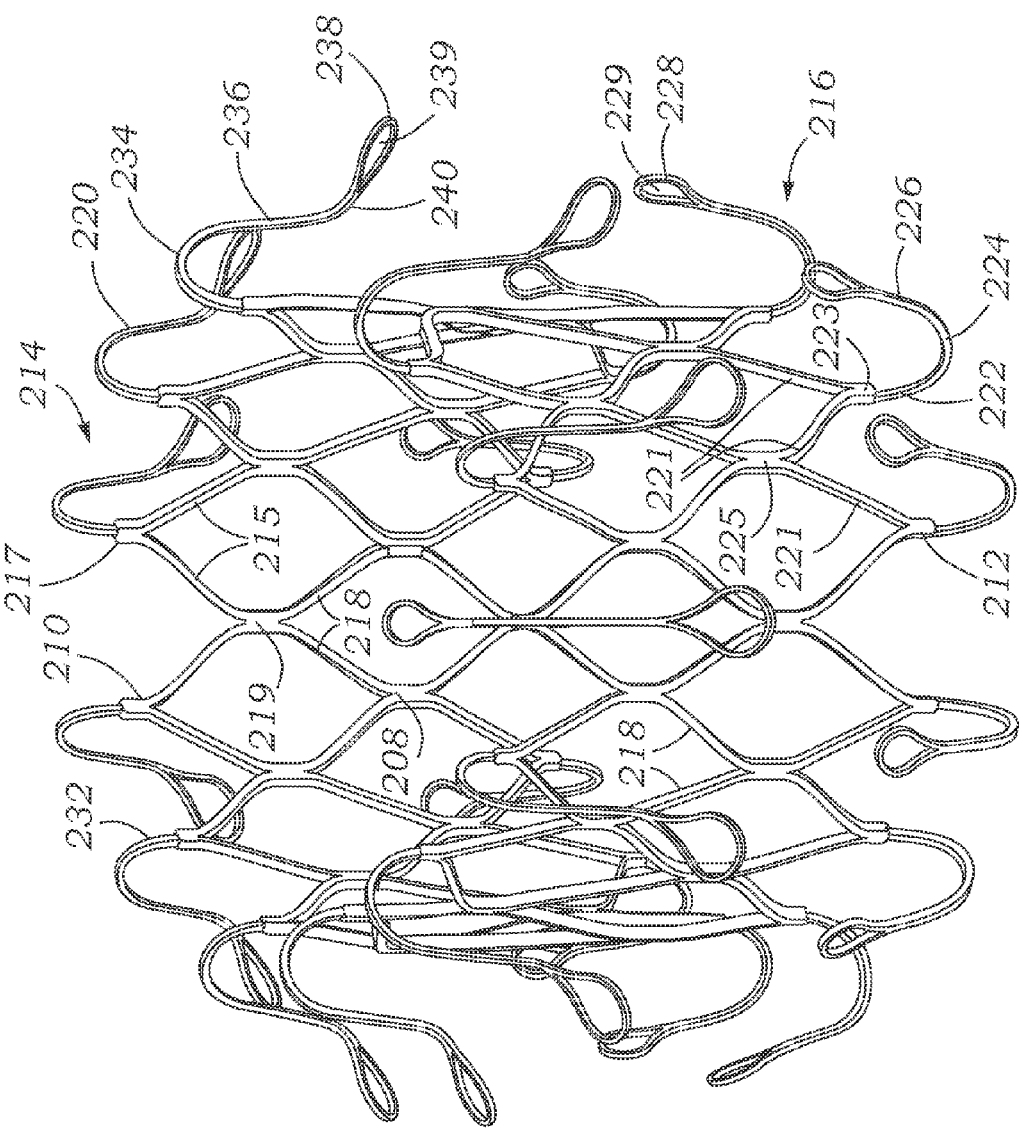
FIG. 7 is a top-sided perspective view of another exemplary frame for use in a prosthetic valve.
Figure 8:
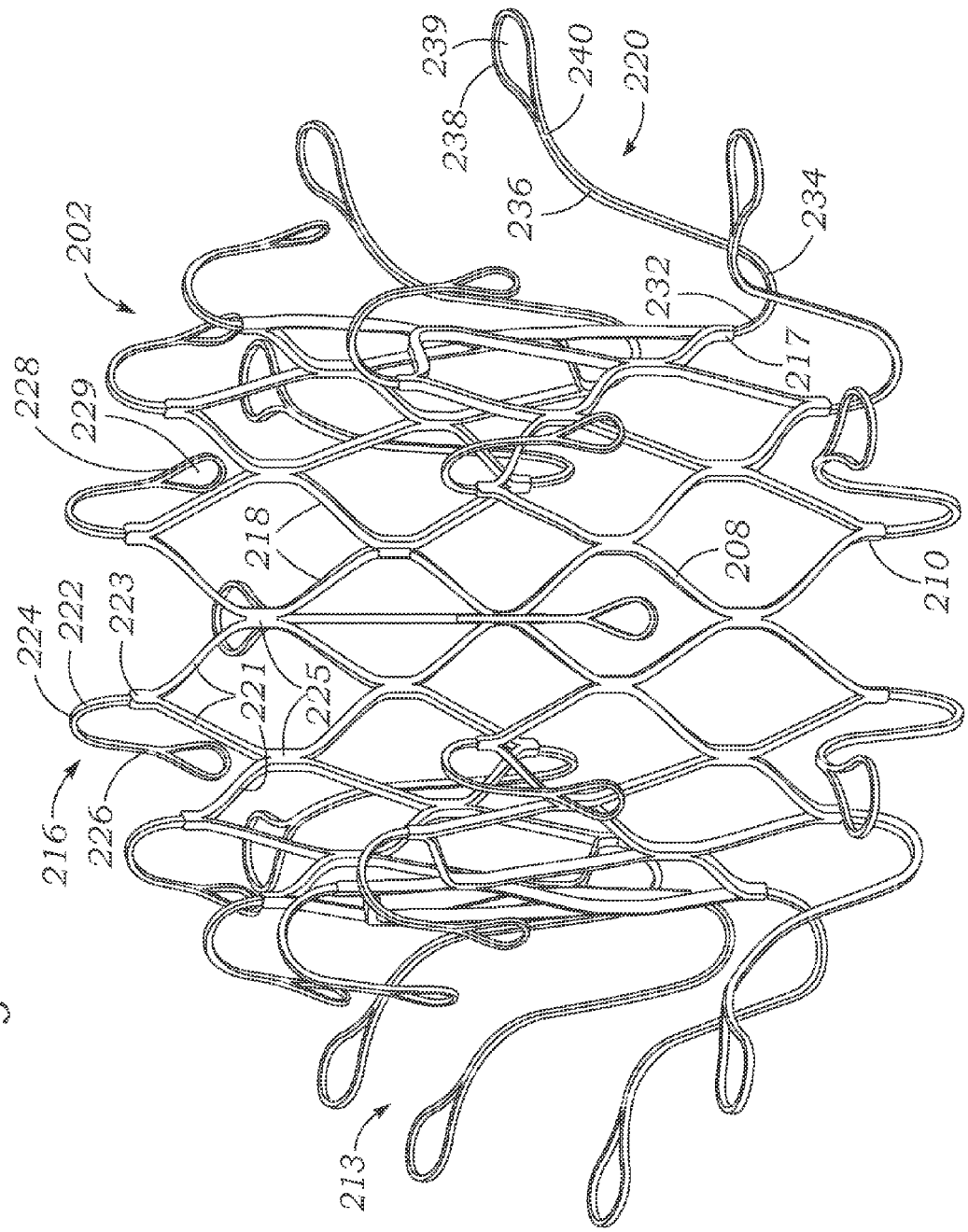
FIG. 8 is a bottom-sided perspective view of the prosthetic valve of FIG. 7.
Figure 10:
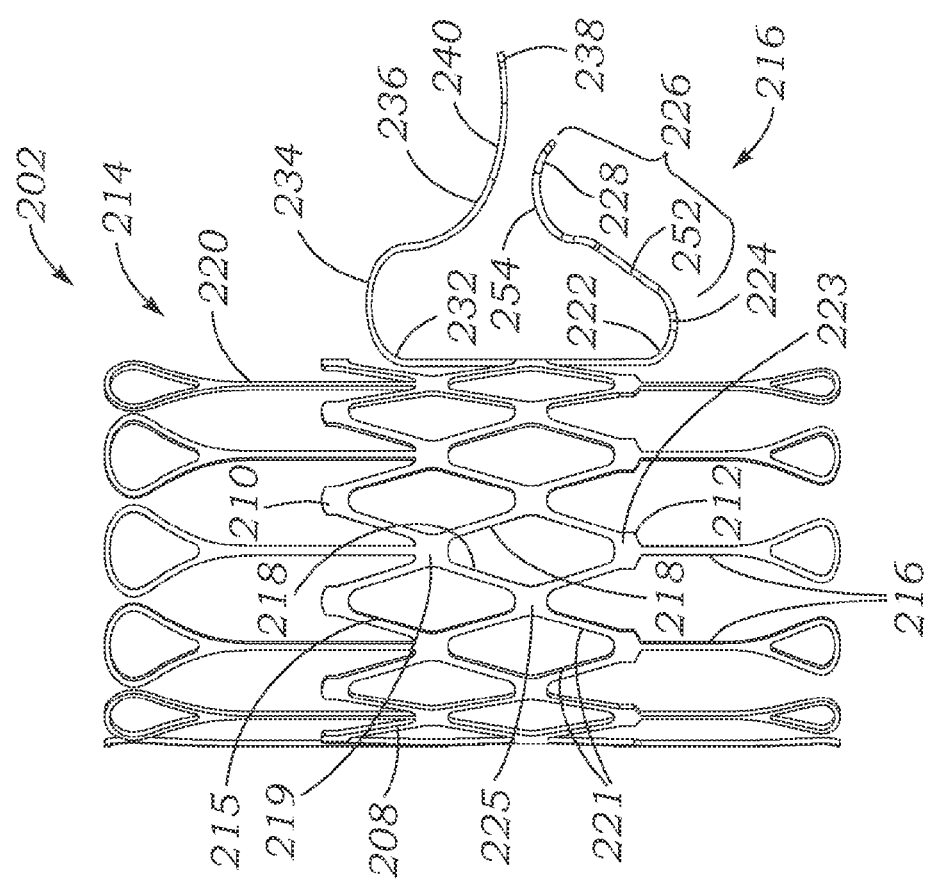
FIG. 10 is a side schematic view of another exemplary frame for use in a prosthetic valve, with a single atrial anchor and a corresponding ventricular anchor shown in a deployed

The atrial anchors 220 can extend generally downwardly from and relative to the atrial end 210 to contact an atrial side of the native valve annulus and/or tissue of the left atrium. Each anchor 220 can extend from an upper row of circumferentially-extending, angled struts 215 at the atrial end 210. In some embodiments, as shown in FIGS. 7-8, the anchors 220 extend outward from the apices 217 of the struts 215 at the atrial end 210. In other embodiments, as shown in FIGS. 9-10, the anchors 220 extend from junctions or nodes 219 at which two adjacent circumferential struts 218 of the second row (from the atrial end 210) intersect the ends of the struts 215 of the uppermost row of struts.

Each atrial anchor 220 can comprise a proximal or fixed end portion 232 connected to the atrial end 210, an intermediate portion 234, and a distal or free end portion 236 that projects radially outwardly from the atrial end 210. The distal end portion 236 can also project downwardly and/or contact the atrial side of the native valve annulus. The proximal end portion 232 can project upwardly from the atrial end 210, and the intermediate portion 234 can comprise a curved portion (or other type of bend) that curves upwardly then downwardly to connect to the distal end portion 236. The distal end portion 236 can comprise a terminal portion 240 having a head portion 238 at its terminus. The head portion 238 can have an opening 239 (such as a teardrop shaped opening as shown) through which atrial and/or native valve annulus tissue can protrude when pressed against the head portion 238 (FIGS. 7-8). Other embodiments of the head portion have another shape, for example, any of the shapes discussed above for the distal head portion 128 of the ventricular anchor. In the illustrated embodiments, an atrial-tissue-contacting face of the head portion 238 is convex, although in other embodiments, the atrial-tissue-contacting face has another shape, for example, substantially planar, concave, convex, or combinations thereof. In the expanded configuration, the terminal portion 240 can splay radially outward relative to the remainder of the distal end portion 236.

The atrial anchors 220 can have a flexible and/or serpentine configuration, or can be substantially stiff. In various embodiments, one or more atrial anchors 220 can comprise a repeating pattern of turns (e.g., such as shown in FIGS. 8A-8C) to enhance the flexibility of the anchors, which can be positioned adjacent to sensitive anatomical structures, such as adjacent to the atrial septum in the vicinity of the native mitral valve annulus. The atrial anchors 220 and/or the spaces between the anchors 220 can be covered by a blood-impermeable fabric or tissue material.

The ventricular anchors 216 can project upward, as described above for frame 102, toward a ventricular side of the native valve annulus (such as to contact the native valve annulus and/or adjacent tissue). Each anchor 216 can have a proximal end portion 222 connected to the ventricular end 212, an intermediate portion 224 having a bend (such as a curve or angle), and a distal end portion 226. As shown in the drawings, each proximal end portion 222 can connect to an apex 223 defined by the intersection of two adjacent circumferential struts 221 of a bottom row of struts of the frame 202 at the ventricular end 212. In alternative embodiments, the proximal end portions 222 of the anchors 216 can connect to nodes or junctions 225 defined by where two adjacent circumferential struts 221 intersect the ends of two struts 218 of a row immediately adjacent the lower most row of struts. The ventricular anchors 216 can have distal end portions 226 with atraumatic head portions 228, which may be curved and/or rounded. These head portions 228 can each have a teardrop-shaped opening 229 through which ventricular tissue and/or native valve annulus tissue can protrude, or can have another shape, for example, any of the shapes discussed above for the distal head portion 128 of the ventricular anchor.

The terminal ends of the fully deployed ventricular anchors 216 can point in a generally upward direction, substantially parallel to the longitudinal axis of the main body 208. As shown in FIG. 9, the distal end portions 226 can each have a first section 252 that extends in an angled direction relative to the main body (upward toward the atrial end 210 and away from the main body 208) and a second section 254, distal to the first section 252, that extends more directly upward (toward and generally parallel to the longitudinal axis of the main body 208). The distal end portions 226 can thereby comprise a bend (such as an angled bend as shown in FIG. 9 or a curved bend) between the first section 252 and the second section 254. As a result, the ventricular anchors 216 can comprise two bends over the intermediate and distal end portions 224, 226. The two bends of the ventricular anchors 216 can, in some cases, facilitate wrapping of the ventricular anchors 216 around the native leaflets. The second section 254 of the distal end portion 226 can comprise the head portion 228 (which can be located at the terminus of the second section 254). In some embodiments, the head portion 228 is configured to extend even more directly upward than the rest of the second section 254.

Referring to FIG. 9A, the first section 252 of the distal end portion 226 extends toward the atrial end 210 at an angle 260 with respect to a line that is parallel to the longitudinal axis of the frame. In particular embodiments, the angle 260 is between about 10 degrees to about 80 degrees, with about 25 degrees being a specific example. The second section 254 extends at an angle 262 relative to the first section 252 in the range of about 100 degrees to about 240 degrees, with about 155 degrees being a specific example.

FIG. 10 shows an alternative embodiment of a second section 254, which is curved to form a rounded (atraumatic) upward-directed surface for contacting the native valve annulus and/or adjacent tissue. This atraumatic portion can be formed by the second section 254 alone, or in conjunction with the head portion 228. Alternatively, the second section 254 can be substantially straight (extending in the same direction as the first segment of the distal end portion 226), and the head portion 228 can be curved to form a rounded portion facing the atrial end 210 (for example, with a contoured side profile as shown in FIG. 7). As in other embodiments, such a curved head portion 228 can have one or more openings 229 through which tissue can protrude.

Figure 11:
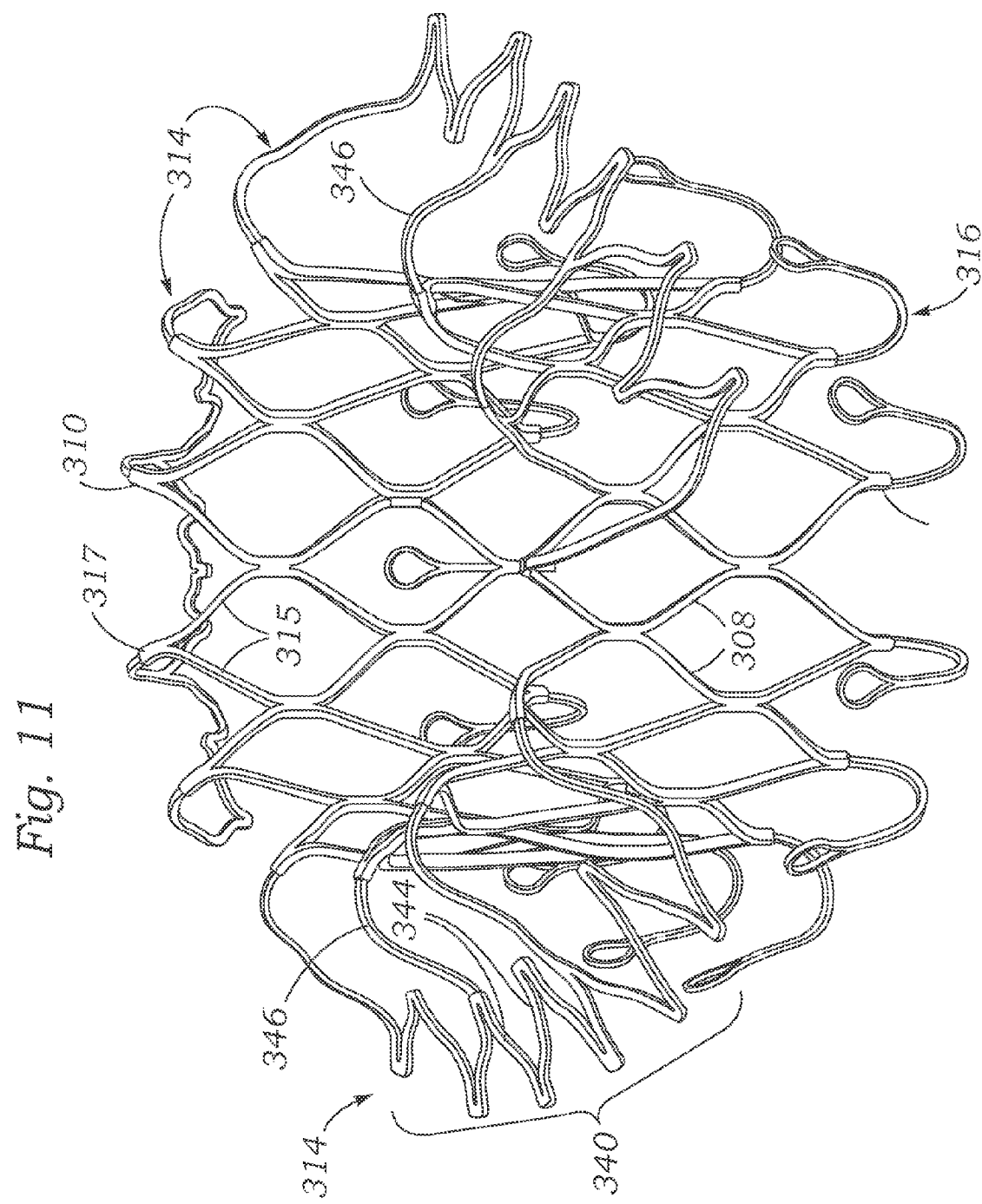
FIG. 11 is a top-sided perspective view of another exemplary frame for use in a prosthetic valve.
Figure 12:
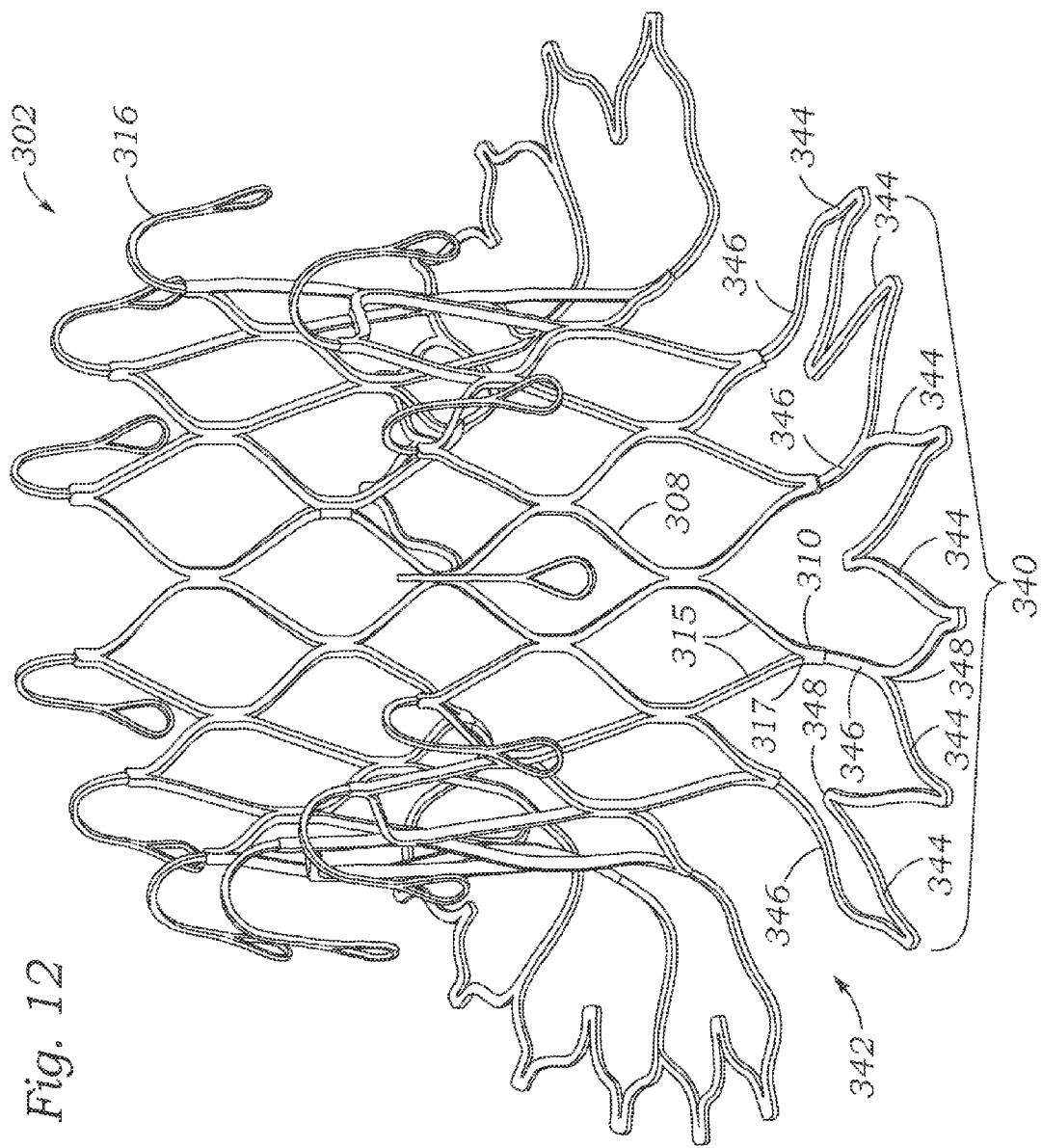
FIG. 12 is a bottom-sided perspective view of the prosthetic valve of FIG. 11.

FIGS. 11-12 show a top perspective view and a bottom perspective view of another exemplary prosthetic valve frame 302 comprising a main body 308, an atrial cap 314 extending radially outward from an atrial end 310 of the main body 308, and a plurality of ventricular anchors 316 extending from a ventricular end 312 of the main body 308. The atrial cap 314 can comprise a stellate pattern, similar to as described above for frame 102. In this embodiment, as shown, the triangular frame elements do not extend uniformly around the circumference of the atrial end 310. Rather, the atrial cap 314 can comprise discrete groups 340 of triangular rim portions 344 that are not directly connected to each other with interconnecting struts.

FIGS. 11-12 show an embodiment having three groups 340 of six triangular rim portions 344. The groups 340 can be spaced angularly apart around the circumference of the atrial end 310. The atrial cap 314 can have open areas 342 in between the groups 340 where there are no triangular rim portions 344 or other atrial cap elements. Each group 340 can have four struts 346, which can be spaced equally apart, connecting the triangular portions 344 to the atrial end 310. In particular, the struts 346 can be connected to apices 317 along a first row of circumferential struts 315 at the atrial end 310. For each group 340, the struts 346 can extend from the main body 308 to the peripheral edges of the outermost triangular portions 344, and from the main body 308 to every other junction 348 of adjacent triangular rim portions 344 (starting from the outer edges of the outermost triangular rim portions). The ventricular anchors 316 can be shaped and configured similar to as described above for frame 202. Other embodiments independently include greater or fewer than three groups of rim portions 344, greater or fewer than four struts 346 per group 340 of rim portions, and or struts that are spaced unequally.

Figure 13:
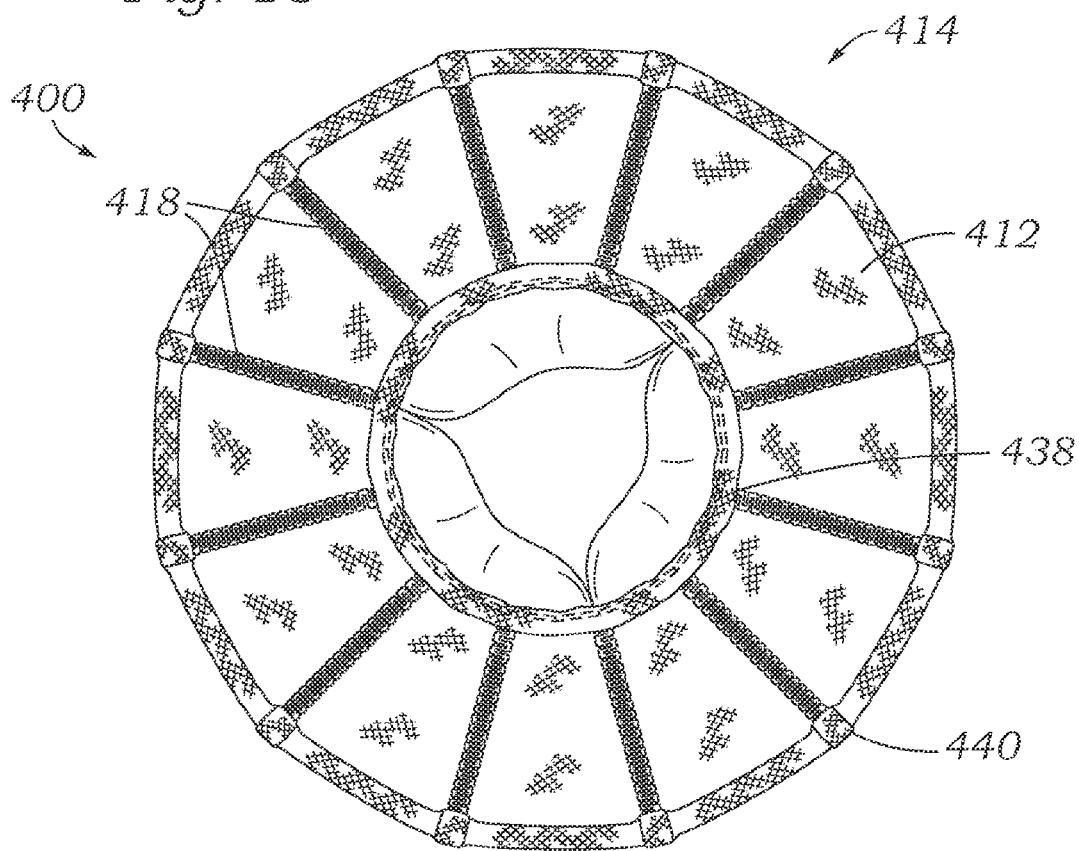
FIG. 13 is a top view of another exemplary prosthetic valve with an atrial cap having serpentine arms.
Figure 14:
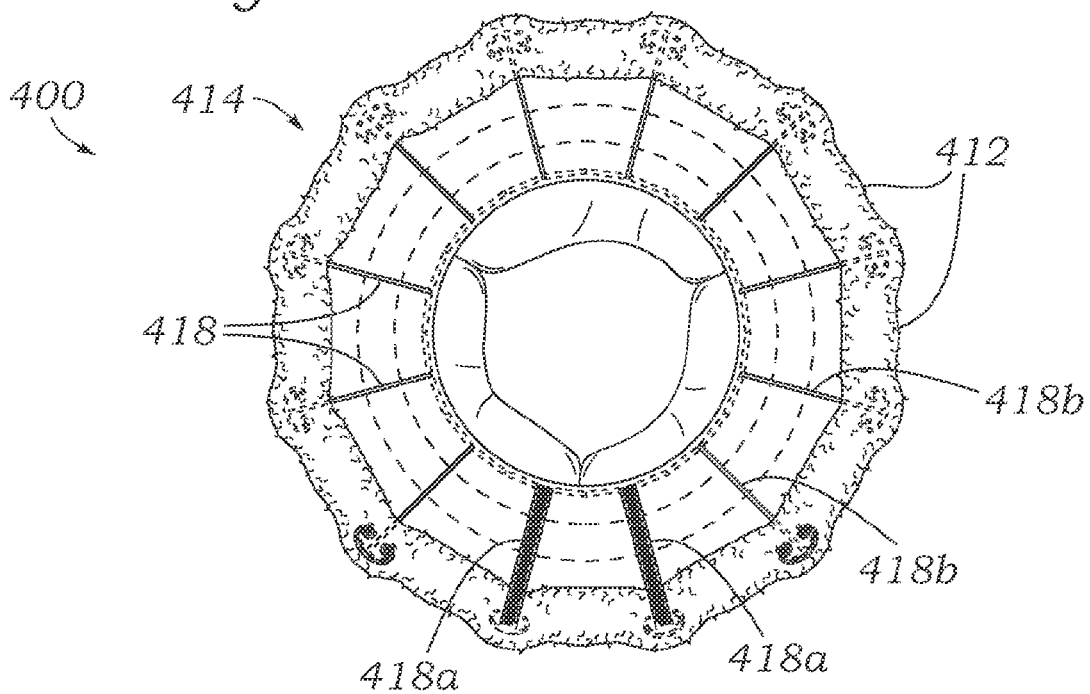
FIG. 14 is a top view of another exemplary prosthetic valve with an atrial cap having a combination of serpentine arms and non-serpentine arms.

FIGS. 13-14 show top views of two additional prosthetic valve embodiments 400, each having an atrial cap member 414 with radially extending arm-like atrial anchors or struts 418. Each arm-like strut 418 extends radially outward from an originating rim portion 438 to an outer rim portion 440. In some cases, as shown in FIG. 13, the struts 418 each have a flexible, serpentine configuration (such as also shown in FIG. 8B). The prosthetic valves 400 can each have at least one layer of fabric or other biocompatible material 412 extending between pairs of struts and covering the terminal portions of each strut 418. In some embodiments, the material layer 412 covers the struts 418 themselves.

In some cases, the distribution and/or composition of the struts 418 is symmetrical (FIG. 13). In some embodiments, the composition of the struts 418 is asymmetrical and can include one or more relatively more flexible struts 418a and one or more less flexible struts 418b. As shown in FIG. 14, the more flexible or distensible struts 418a can be concentrated in one area. For example, the struts which face the atrial septum and/or abutting other sensitive structures (native or foreign) can be more flexible and/or more distensible relative to the other struts. In alternative embodiments, the struts 418 can have any of configurations described above for the ventricular anchors in connection with FIGS. 8A-8C.

Delivery Techniques and Assemblies

In some cases, for safety and/or other reasons, the disclosed prosthetic devices may be delivered from the atrial side of the atrioventricular valve annulus. Delivery from the atrial side of the native valve annulus can be accomplished in various manners. For example, a transatrial approach can be made through an atrial wall, which can be accessed, for example, by an incision through the chest. Atrial delivery can also be made intravascularly, such as from a pulmonary vein. The prosthetic valve can be delivered to the right atrium via the inferior or superior vena cava. In some cases, left atrial delivery can be made via a transeptal approach (FIGS. 16A-16D). In a transeptal approach, an incision can be made in the atrial portion of the septum to allow access to the left atrium from the right atrium. The prosthetic valve can also be delivered via transventricular (FIG. 19), transatrial (FIG. 17), or transfemoral (FIG. 18) approaches with small or minimal modifications to the delivery process.

To deliver the prosthetic valve to the native mitral valve annulus, the prosthetic valve can be radially crimped into a collapsed configuration within a sheath of a delivery catheter. Delivery and placement of the prosthetic valve can be angularly independent, such that the prosthetic valve does not require any special rotational alignment relative to the axis of the prosthetic valve. Thus, during delivery, the prosthetic valve may not require any special rotational placement so as to align the ventricular anchors with particular anatomical landmarks (such as the native valve leaflets, particular portions thereof, native valve commissures, chordae tendineae, and/or location of the aortic valve).

While in certain embodiments, the prosthetic valve is positioned such that certain atrial and/or ventricular arms or anchors face sensitive structures (such as the atrial or ventricular septum), this positioning can be approximate and may not necessarily require precise rotational alignment. Thus, such a positioning will generally not require the user to exert a considerable effort achieving a particular rotational alignment for the valve.

In some embodiments, the prosthetic valve can fit inside of a 30 French (F) catheter (in a collapsed state). In some embodiments, the prosthetic valve can be configured to fit into even smaller catheters, such as a 29 F, 28 F, 27 F, or 26 F catheter.

FIGS. 15A-15C show an exemplary prosthetic valve delivery assembly, including the process of expanding the prosthetic valve using a sheath, with reference to an embodiment of the prosthetic valve using the frame illustrated in FIG. 4, although the delivery assembly and method are applicable to each of the frame embodiments disclosed herein. In the delivery configuration (FIG. 15A), a retractable sheath 502 of a delivery catheter 500 can be advanced over the collapsed prosthetic valve, with the main body 108, atrial cap 114 (not shown) and ventricular anchors 116 all in a radially collapsed configuration. The ventricular anchors 116 can be contained within the sheath 502 in a substantially linear arrangement, distal to the main body 108, such that the distal end portions 126 are axially aligned with the intermediate portions 124 and the proximal end portions 122. Thus, while the distal end portions 126 may be biased to extend upward (in the direction of the main body 108) when deployed, the constraining or restraining force applied by the sheath 502 on the anchors 116 can force the distal end portions 126 to extend downward (away from the main body 108 in a generally apical direction) during delivery.

Once the prosthetic valve 100 is delivered to the native annulus region, the sheath 502 can be retracted relative to the prosthetic valve 100, thereby allowing the prosthetic valve 100 to expand radially outward. The release of the prosthetic valve 100 can be conducted in stages. In particular, the ventricular anchors 116 can be released from the sheath 502 (FIG. 15B) prior to the release of the main body 108 (FIG. 15C). As shown in FIG. 15B, when the ventricular anchors 116 are released, the anchors 116 can spread out away from the main body 108, with distal end portions 126 directed radially outward and upward. Then, with release of the main body, the anchors 116 can rotate toward the main body 108, such that the distal end portions 126 can pivot toward the vertical (longitudinal) axis and wrap around the native leaflets.

Figure 16A:
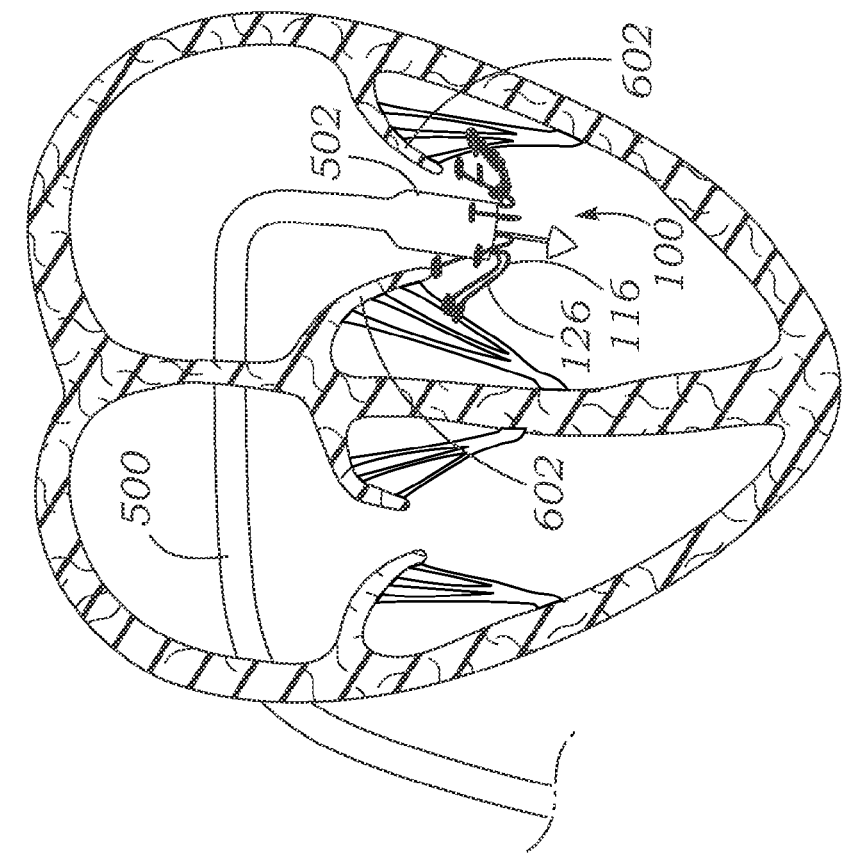
Figure 16B:
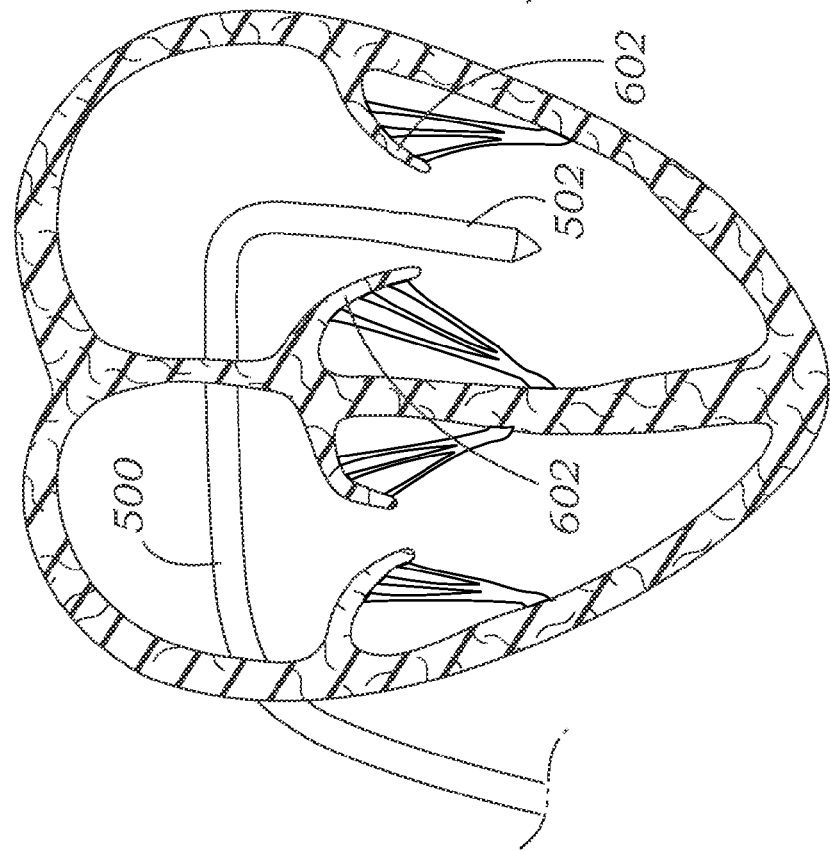
Figure 17:
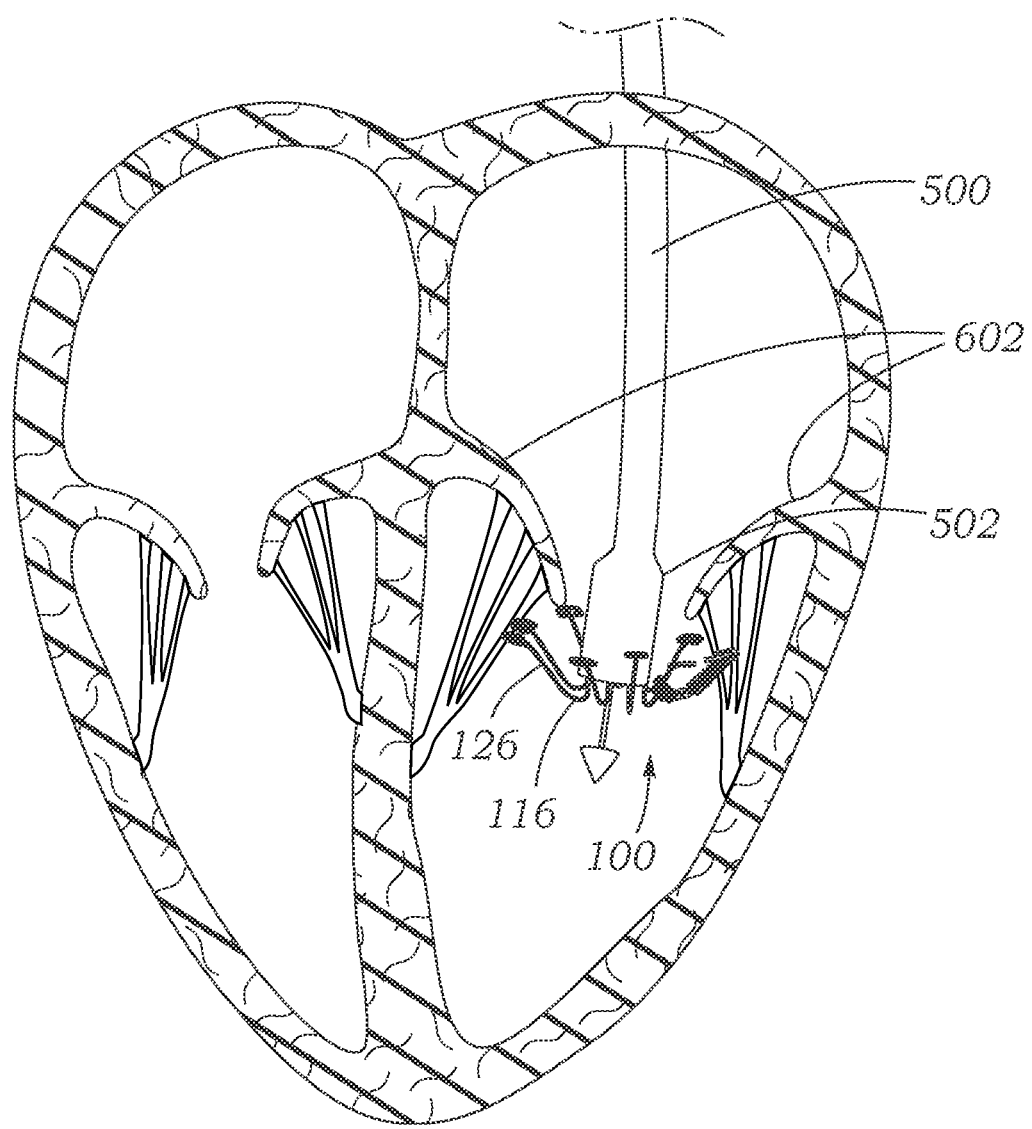
FIG. 17 shows another exemplary method for implanting a prosthetic valve at the mitral valve annulus region, via a transatrial approach.

FIGS. 16A-16D show the process of delivering the prosthetic valve assembly to the native mitral valve annulus, according to one embodiment. FIG. 16A shows the catheter 500 (carrying the prosthetic valve 100 within the sheath 502 at its distal end) introduced into the right atrium of the heart, then across the atrial septum and into the left atrium. The catheter 500 can be further advanced such that the sheath 502 (carrying the prosthetic valve) extends between the native leaflets of the mitral valve and into the left ventricle. At this point, the prosthetic valve 100 can be advanced out of the distal end of the sheath 502, such as by advancing a pusher device distally against the prosthetic valve and/or retracting the sheath 502 relative to the prosthetic valve 100, resulting in the deployment of the ventricular anchors 116 (FIG. 16B).

As shown in FIG. 16B, the deployed ventricular anchors 116 can extend radially outwardly behind the native leaflets 602. The surgeon or other user can then optionally reposition the partially retracted valve 100 as desired, then retract the sheath 502 further to cause the ventricular anchors 116 to engage the native valve annulus (FIG. 16C). In particular, the anchors 116 can be configured to point more directly upward upon full deployment, as compared to when they are partially deployed from the sheath 502. At this point, the user can assess engagement of the ventricular anchors 116 with the native valve annulus (such as through imaging means), prior to retracting the sheath 502 further to deploy the main body 108 and the atrial cap 114 (FIG. 16D). As shown in FIGS. 16C-16D, the ventricular anchors 116 can progressively pivot with deployment of the main body 108, such that the distal end portions 126 pivot or rotate to point more directly upward.

The head portions 128 of the upward directed distal end portions 126 can contact a ventricular side of the native valve annulus and/or adjacent tissue (such as trigone areas) (FIG. 16D). In some cases, however, at least one of the ventricular anchors 116 does not reach the native valve annulus or adjacent tissue, but can nonetheless produce stable placement of the prosthetic valve 100. For example, in some cases, the at least one ventricular anchor 116 can produce this stable placement at the native valve annulus region by engaging the chordae tendineae below the native valve annulus.

Figure 20:
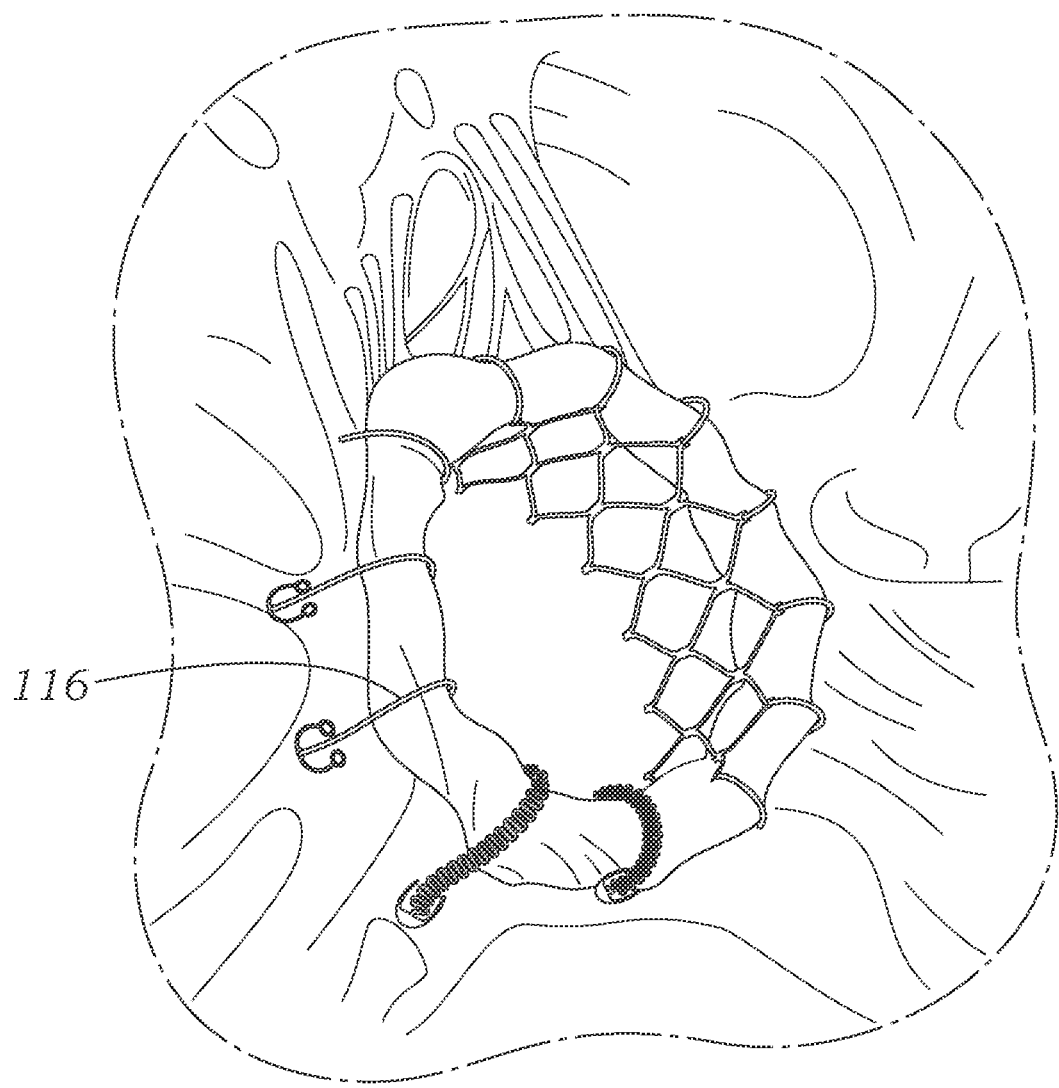
FIG. 20 illustrates the ventricle side of a native mitral valve having ventricular anchors that engage the tissue of the native valve, creating a seal against the outer surface of the main body of the frame. The prosthetic leaflets and material layers are omitted for clarity of illustration.

In some implementations, one or more ventricular anchors 116 engage the chordae tendineae, one or more ventricular anchors engage the trigone areas, and/or one or more ventricular anchors engage the native leaflets at A2 and/or P2 positions (i.e., between the commissure of the native leaflets). The ventricular anchors that engage the native leaflets and the trigone areas can capture or "sandwich" the native tissue between the outer surface of the main body of the prosthetic valve and the ventricular anchors (or portions thereof) such that the tissue is compressed and engaged by the main body of the prosthetic valve on one side and by the ventricular anchors on the other side. In some embodiments, due to the capturing of the native tissue (such as the native leaflets) between the ventricular anchors and the main body, the native tissue forms a seal around the main body (through 360 degrees) within the left ventricle that impedes blood from traveling along the outside of the main body (as best shown in FIG. 20). In some embodiments, tissue is also or alternatively sandwiched between the atrial cap 114 and ventricular anchors 116. By virtue of their relatively thin profile and because the ventricular anchors are not interconnected to each other, the distal ends of the ventricular anchors adjacent the chordae tendineae can pass between individual chords extending from the native leaflets, allowing those anchors to flex/pivot upwardly and assume their fully deployed positions.

Finally, as shown in FIG. 16D, the sheath 502 can be retracted further to release the atrial cap 114. The atrial cap 114 forms a seal against the native annulus within the left atrium. The seal created in the left atrium by the atrial cap 114 and the seal created by the ventricular anchors 116 in the left ventricle together prevent, reduce, or minimize the flow of blood between the native annulus and the outside of the main body 108 during diastole and systole. In some embodiments, the main body 108 and the atrial cap 114 are released simultaneously, while in other embodiments, the main body 108 is released prior to the atrial cap 114. Upon full deployment of the ventricular anchors 116 and the main body 108, the distal end portions 126 can be positioned against the native valve annulus and/or adjacent tissue (e.g., trigone areas). All stages of deployment of the prosthetic valve 100 can thus be controlled by the catheter 500 without additional activation or manipulation necessary. In certain embodiments, however, the prosthetic valve 100 and/or the catheter 500 can comprise a switch or other control to regulate the release and/or subsequent movement of ventricular anchors 116 or the main body 108.

Figure 18:
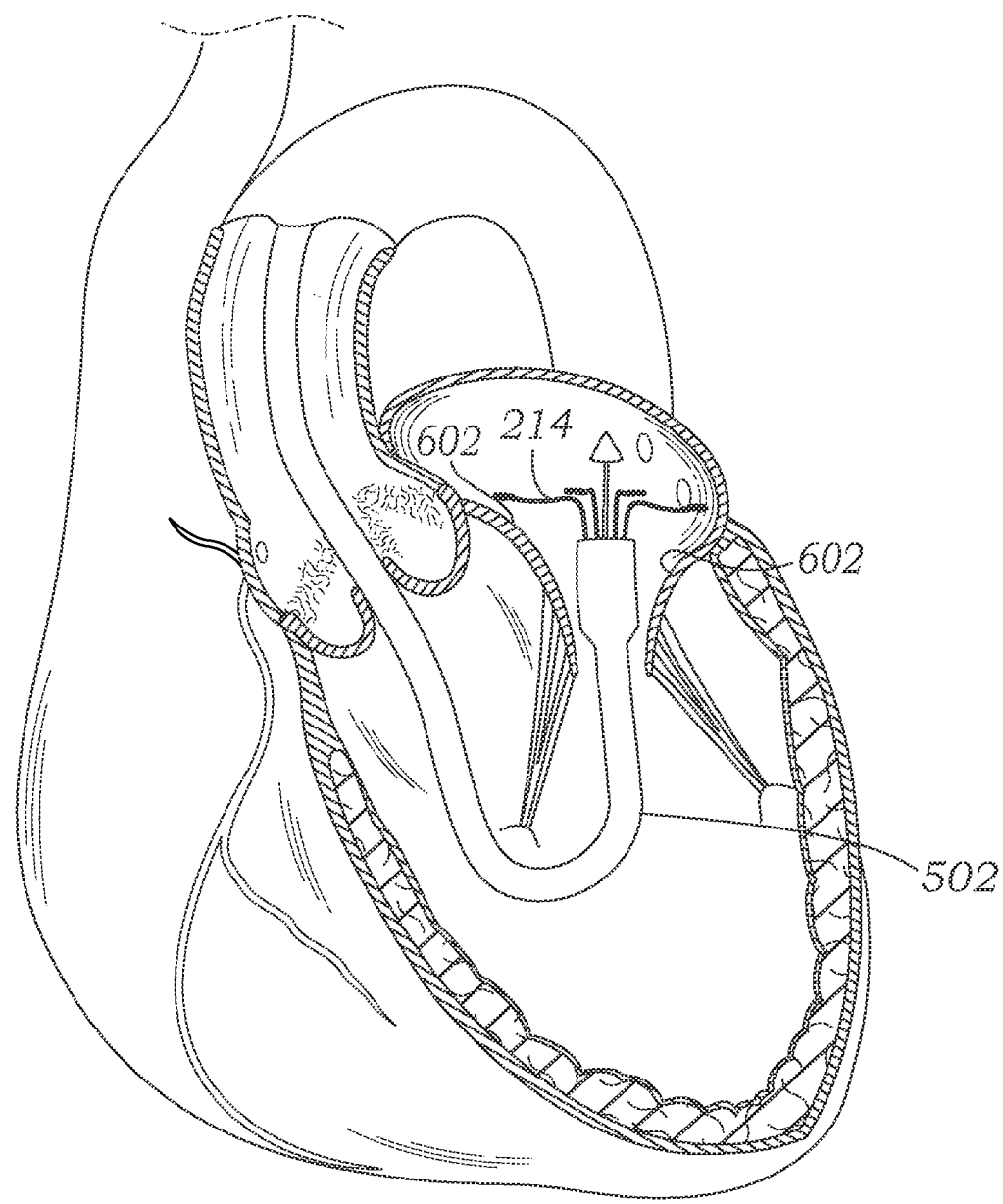
FIG. 18 shows another exemplary method for implanting a prosthetic valve at the mitral valve annulus region, via a transfemoral approach.
Figure 19:
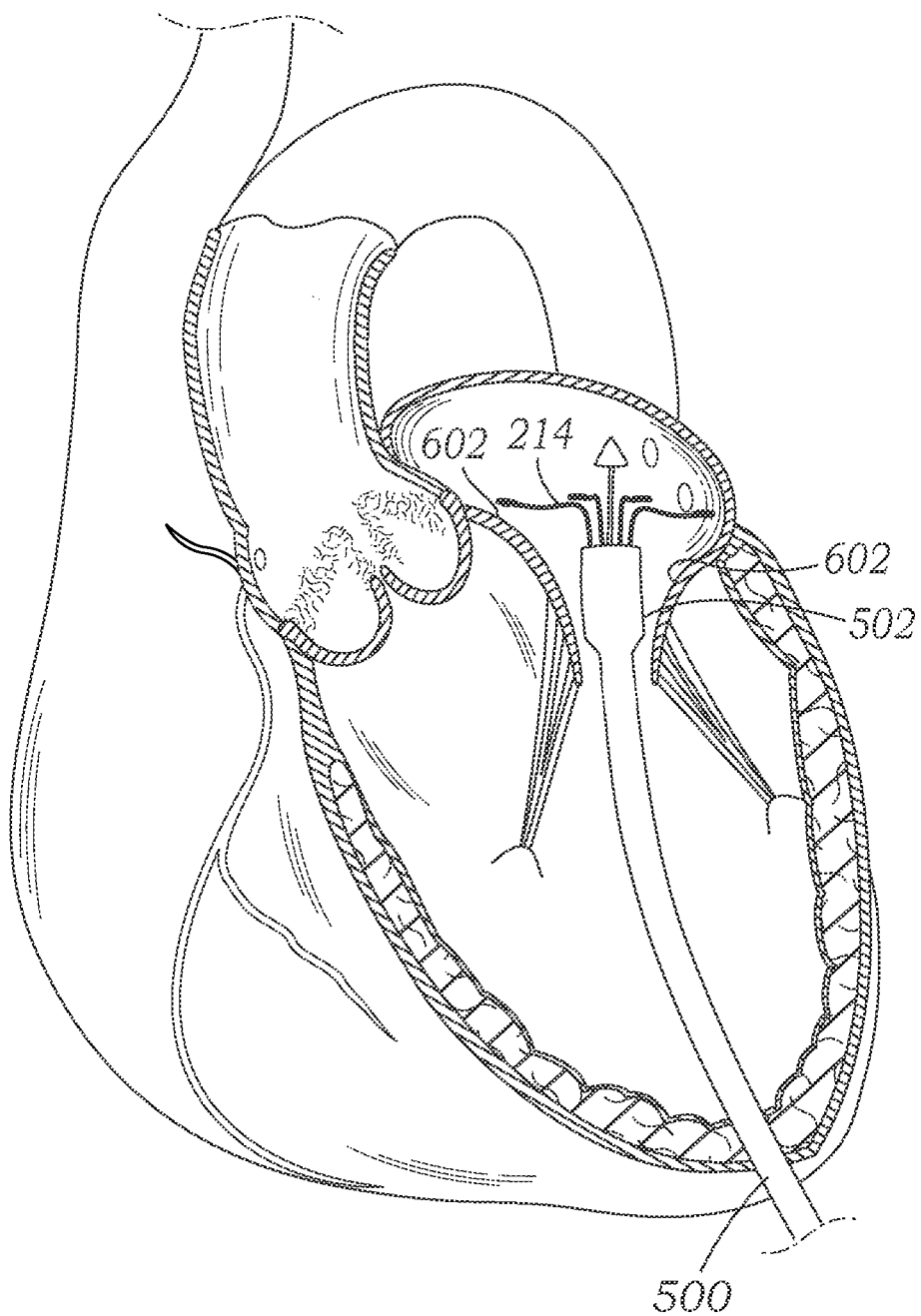
FIG. 19 shows another exemplary method for implanting a prosthetic valve at the mitral valve annulus region, via a transventricular approach.

In alternative embodiments, the prosthetic valve 100 can be delivered to the native mitral valve via the left ventricle (FIGS. 18-19). FIGS. 18-19 illustrate deliveries and deployments of embodiments of prosthetic valves incorporating the frame illustrated in FIGS. 7 and 8, but the assemblies and methods are applicable to prosthetic valves including any of the frames disclosed herein. In a transventricular approach (FIG. 19), for example, the delivery catheter 500 can be inserted into the left ventricle through a surgical incision made at or near the bare spot on the lower anterior ventricle wall. In this approach and in the transfemoral approach (FIG. 18), the prosthetic valve 100 can be loaded into the sheath 502 in the reverse position such that the atrial cap 214 is closest to the distal end of the sheath. During implantation, the atrial cap 214 can be deployed first, followed by the main body 208 (FIGS. 7-8) and the ventricular anchors 216.

In various embodiments, portions of the prosthetic valve 100 can be partially or fully recaptured during the delivery process entirely through manipulation of the sheath 502. The ability to recapture the prosthetic valve 100 can be advantageous, for example, in case of damage to the prosthetic valve 100 during delivery and/or in case of operator error in placement of the prosthetic valve 100. In some embodiments, the ventricular anchors 116 can be recaptured following release from the sheath 502, simply by advancing the sheath 502 over the deployed anchors 116, thereby bringing the anchors 116 back into a linear configuration within the confines of the sheath 502. In some embodiments, the main body 108 can also be recaptured, also by advancing the sheath 502 over the deployed body 108.

Some embodiments of the delivery system include an inner sheath, located within the sheath 502, which contains the main body 108 and the atrial cap 114 but does not contain the ventricular anchors 116. In this case, the sheath 502 can be fully retracted to release the ventricular anchors 116, with release of the main body 108 and atrial cap 114 controlled by retraction of the inner sheath.

Figure 21:
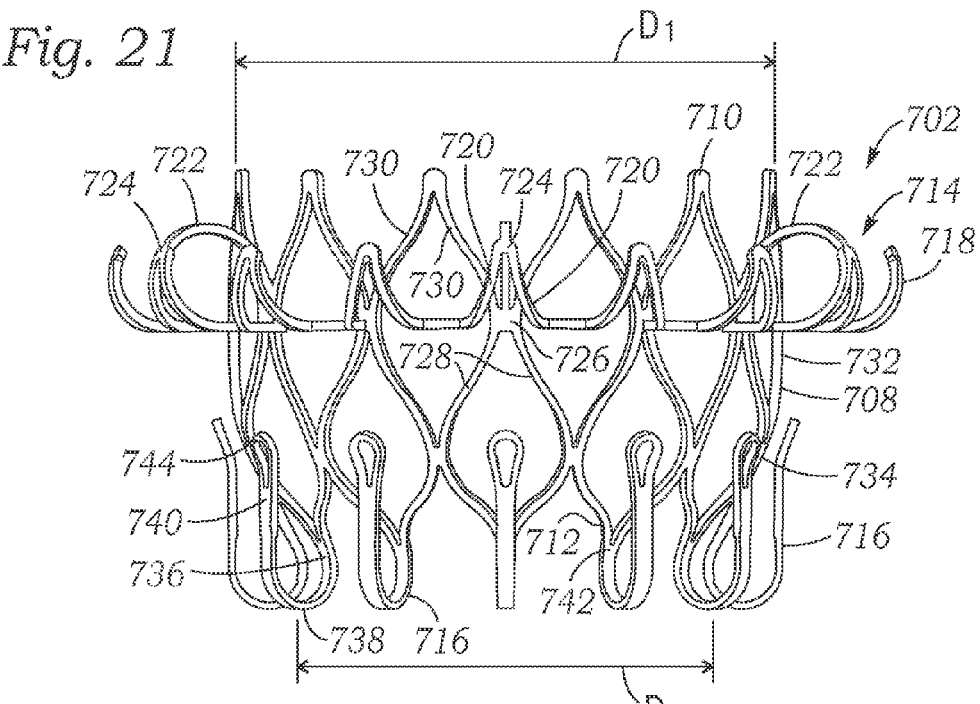
FIG. 21 shows a side elevation view of another exemplary embodiment of a frame for a prosthetic valve.

FIG. 21 is a side elevation view of another prosthetic valve frame 702 that can be implemented in a prosthetic valve. The frame 702 comprises an annular main body 708, an atrial cap 714 extending radially outward from the atrial end 710 of the main body, and a plurality of ventricular anchors 716 extending from the ventricular end 712 of the main body. The atrial cap 714 can comprise a continuous annular rim 718 formed from a plurality of circumferentially extending angled struts 720. The atrial cap 714 can comprise a plurality of radially extending connecting struts 722. Each connecting strut 722 has a first end connected to an apex 724 of two struts 720 and a second end connected to an apex 726 of two angled struts 728 of the main body 708.

As can be seen in FIG. 21, the second ends of the connecting struts 722 are connected to the apices 726 of struts 728 that form a row of circumferentially extending struts adjacent the uppermost row of struts 730 that form the atrial end 710 of the main body. In this manner, when the frame 702 is deployed from a delivery sheath, the atrial cap 714 curls or deflects downwardly below the atrial end 710 toward the ventricular end 712, which assists in pushing the prosthetic valve further upwardly into the left atrium to minimize obstruction of the left ventricular outflow tract (LVOT). In particular embodiments, the entire atrial cap 714 is spaced below the atrial end 710 of the main body 708. In alternative embodiments, the connecting struts 722 can be connected to the apices of struts 730 that form the atrial end 710 of the main body 708.

The main body 708 can have an overall tapered shape defining an inlet diameter $D_1$ at the atrial end 710 and a smaller outlet diameter $D_2$ at the ventricular end 712. In the illustrated embodiment, the main body 708 comprises a first, substantially cylindrically-shaped inlet portion 732 defining the inlet diameter and a second, conically-shaped outlet portion 734 defining the outlet diameter, which tapers in a direction extending from the lower end of the inlet portion 732 toward the ventricular end 712 of the main body. The inlet end portion 732 can be relatively large and oversized relative to the native mitral valve annulus to establish a good seal between the outer surface of the prosthetic valve and the native leaflets 602 to prevent or minimize paravalvular leakage while the relatively smaller outlet end portion 734 prevents or minimizes obstruction of the LVOT. In certain embodiments, the inlet diameter $D_1$ of the inlet end portion 732 is at least about 30 mm to about 50 mm, with about 40 mm being a specific example, while the outlet diameter $D_2$ of the outlet end portion 732 is about 20 to about 40, with about 30 mm being a specific example.

Each ventricular anchor 716 can have a fixed end portion 736 connected to the ventricular end 712 of the main body, an intermediate portion 738 having a bend, and a free end portion 740. As shown in the drawings, each fixed end portion 736 can be connected to an apex 742 formed by two angled struts at the ventricular end 712 of the main body. The free end portions 740 can have atraumatic head portions 744, which may be curved and/or rounded. The head portions 744 can each have a teardrop-shaped opening through which ventricular tissue and/or native valve annulus tissue can protrude, or can have another shape, for example, any of the shapes discussed above for the distal head portion 128 of the ventricular anchor.

The ventricular anchors 716 are relatively wide and stiff in the lateral direction to minimize side-to-side movement of the anchors to permit crimping and deployment without the anchors becoming entangled with each other. To minimize axial stiffness (to facilitate crimping and deployment), the thickness of the intermediate portions 738 can be reduced relative to other portions of the anchors 716 and the main body 708. In certain embodiments, for example, the intermediate portions 738 can be thinner than the fixed end portions 736, the free end portions 740, and the main body 708.

Figure 22:
FIG. 22 shows a side view of a metal tube for forming the frame of FIG. 21, shown with an area of reduced thickness that forms a portion of the ventricular anchors.
Figure 23:
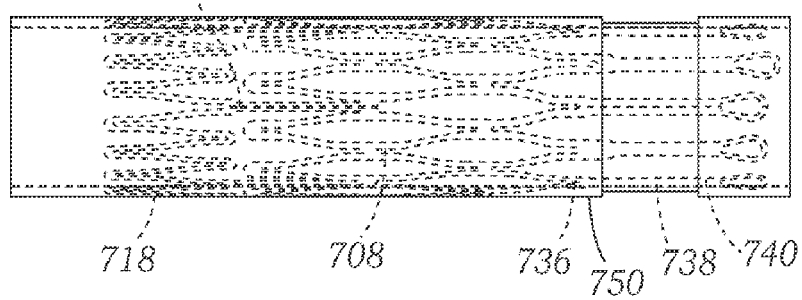
FIG. 23 shows the tube of FIG. 22 and a pattern for laser cutting the frame from the tube.

FIGS. 22 and 23 show one technique for forming a frame 702 with ventricular anchors 716 having a reduced thickness. FIG. 22 shows a metal tube 750 (e.g., a Nitinol tube) for forming the frame 702. The tube 750 is treated by, for example, machining, grinding, or electro-polishing, to produce a recessed portion 752 having a reduced thickness relative to the remainder of the tube 750. FIG. 23 shows the pattern for laser cutting the frame 702 from the tube 750. As can be seen, the intermediate portions 738 are formed from the recessed portion 752 of the tube such that the finished frame (fully cut from the tube) is thinner along the intermediate portions 738 compared to the remainder of the frame.

Figure 24:
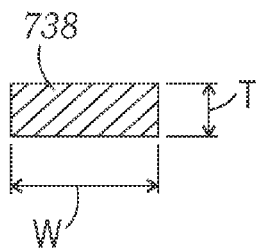
FIG. 24 shows a cross-sectional view of a ventricular anchor of the frame of FIG. 21.

FIG. 24 shows a cross-section of a ventricular anchor 716 taken through the intermediate portion 738. In certain embodiments, the anchors 716 have width W of about 0.8 mm to about 2.0 mm, with about 1.4 mm being a specific example. The width W can be constant along the entire length of the anchor. In certain embodiments, the intermediate portions 738 of the anchors have a thickness T of about 0.4 mm and the remainder of the frame 702 (including the fixed end portions 736 and the free end portions 740 of the anchors) can have a thickness of about 0.5 mm.

Figure 25:
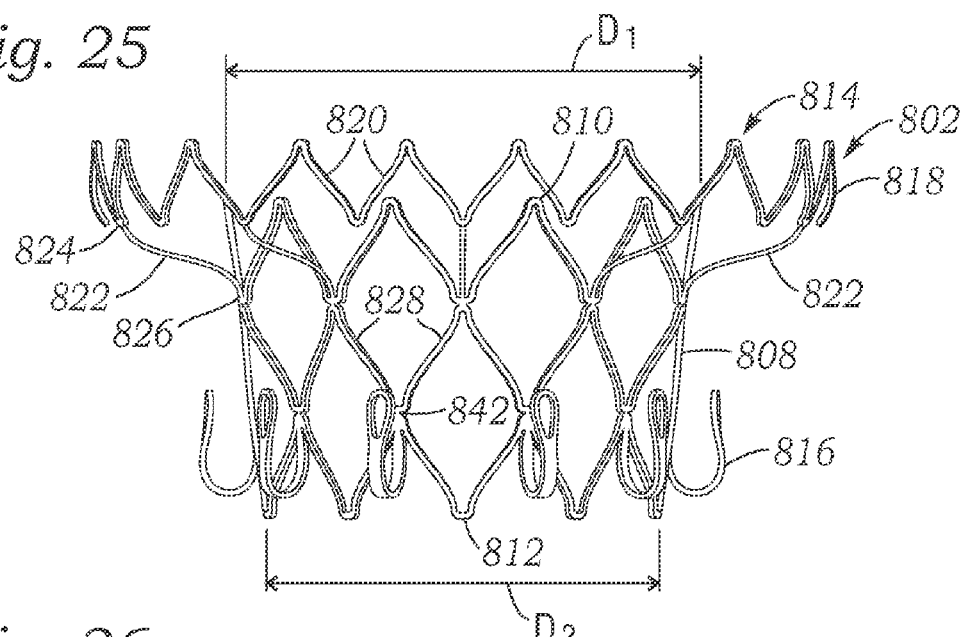
FIG. 25 shows a side elevation view of another exemplary embodiment of a frame for a prosthetic valve.
Figure 26:
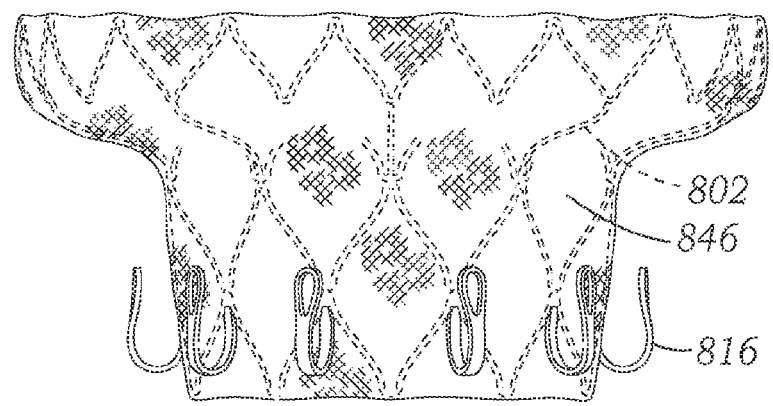
FIG. 26 shows the frame of FIG. 25 covered by an outer skirt.

FIG. 25 is a side elevation view of another prosthetic valve frame 802 that can be implemented in a prosthetic valve. FIG. 26 shows the frame 802 covered by an outer skirt or sealing member 846. The frame 802 comprises an annular main body 808, an atrial cap 814 extending radially outward from the atrial end 810 of the main body, and a plurality of ventricular anchors 816 extending from the main body at a location proximate the ventricular end 812 of the main body. The atrial cap 814 can comprise a continuous annular rim 818 formed from a plurality of circumferentially extending angled struts 820. The atrial cap 814 can comprise a plurality of radially extending connecting struts 822. Each connecting strut 822 has a first end connected to an apex 824 of two struts 820 and a second end connected to an apex 826 of two angled struts 828 of the main body 808, spaced from the atrial end 810 of the main body. In alternative embodiments, the connecting struts 822 can be connected to the apices at the atrial end 810 of the main body.

The main body 808 can have an overall tapered or conical shape defining an inlet diameter $D_1$ at the atrial end 810 and a smaller outlet diameter $D_2$ at the ventricular end 812. In certain embodiments, the inlet diameter $D_1$ is at least about 30 mm to about 50 mm, with about 40 mm being a specific example, while the outlet diameter $D_2$ is about 20 to about 40, with about 30 mm being a specific example.

Each ventricular anchor 816 can have a fixed end portion 836 connected to the main body, an intermediate portion 838 having a bend, and a free end portion 840. As shown in the drawings, each fixed end portion 836 can be connected to an apex 842 formed by two angled struts 828 forming a row of struts spaced from the ventricular end 812 of the main body. Mounting the ventricular anchors 816 at a location closer toward the atrial end reduces the distance between atrial cap 814 and the ventricular anchors to enhance anchoring of the prosthetic valve. In addition, the ventricular anchor 816, being spaced from the ventricular end 812 of the main body, are mounted to a relatively stiff region of the frame to minimize distortion of the frame during crimping and deployment. In alternative embodiments, the ventricular anchors 816 can be connected to the apices at the ventricular end 812 of the main body.

The free end portions 840 of the ventricular anchors can have atraumatic head portions 844, which may be curved and/or rounded. The head portions 844 can each have a teardrop-shaped opening through which ventricular tissue and/or native valve annulus tissue can protrude, or can have another shape, for example, any of the shapes discussed above for the distal head portion 128 of the ventricular anchor.

Figure 27:
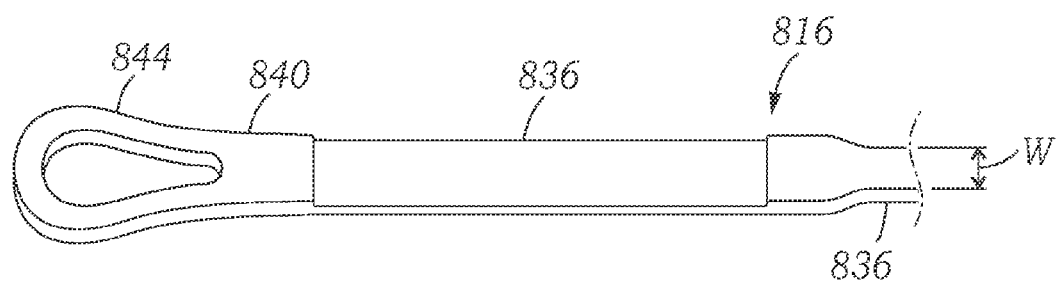
FIG. 27 is an enlarged, perspective view of a ventricular anchor of the frame of FIG. 25.

As best shown in FIG. 27, the fixed end portion 836 of each ventricular anchor 816 can be tapered such that the fixed end portion is reduced in width W where it is connected to an apex 842 to enhance flexibility of the connection between the anchors and the main body. The intermediate portion 838 of each anchor can have a reduced thickness T relative to other portions of the anchors 816 and the main body 808 to minimize axial stiffness of the anchors.

General Considerations

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and subcombinations with one another. The methods, devices, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B", "C", "A and B", "A and C", "B and C", or "A, B, and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Rather, the scope of the invention is at least as broad as the following exemplary claims. We therefore claim at least all that comes within the scope of the following claims.

We claim:

1. A prosthetic device for implanting at a native mitral or tricuspid valve region of the heart, the native valve region having a native valve annulus and native leaflets, the prosthetic device comprising:
   a main body configured for placement within the native valve annulus, the main body having a lumen extending between an atrial end and a ventricular end and a longitudinal axis extending from the atrial end to the ventricular end;
   an atrial cap that extends radially outwardly from the atrial end; and
   a plurality of ventricular anchors spaced angularly around a circumference of the main body, each ventricular anchor having a proximal end portion connected to the main body proximate the ventricular end at only one location on the main body, an intermediate portion extending away from the atrial end and then back toward the atrial end so as to define a first bend, and a distal end portion extending from the intermediate portion, the distal end portion comprising a first section, and a second section, the first section extending from the intermediate portion alongside the main body between the atrial end and the ventricular end in a direction toward the atrial end and radially away from the main body at a first angle relative to the longitudinal axis starting at the intermediate portion and moving toward the second section of the distal end portion, the second section extending from the first section in a direction radially away from the main body at a second angle relative to the longitudinal axis starting at the first section and moving toward a distal end of the second section, the second angle being greater than the first angle, the second section comprising a tissue-engaging surface facing the atrial end that can contact the native annulus and/or the native leaflets, the second section being wider in a circumferential direction along the tissue-engaging surface than the proximal end portion and the intermediate end portion.

2. The prosthetic device of claim 1, wherein at least one of the ventricular anchors comprises a pattern of repeating turns.

3. The prosthetic device of claim 2, wherein the pattern of repeating turns comprises a serpentine, coiled, or helical pattern.

4. The prosthetic device of claim 1, wherein the atrial cap comprises a plurality of atrial anchors spaced angularly around a circumference of the main body, each atrial anchor having a proximal end portion connected to the atrial end and a free distal end portion.

5. The prosthetic device of claim 1, wherein the plurality of ventricular anchors is radially compressible to a radially compressed state for delivery into the heart, wherein each anchor is linearly extended in the radially compressed state, such that the proximal end portions and distal end portions are axially aligned, parallel to the axis of the main body.

6. The prosthetic device of claim 1, wherein the plurality of ventricular anchors is connected to the main body independently of each other without frame segments interconnecting adjacent ventricular anchors.

7. The prosthetic device of claim 6, wherein for each ventricular anchor, the location where the proximal end portion is connected to the main body is the only location where the ventricular anchor is fixed to the main body.

8. The prosthetic device of claim 1, wherein each of the second sections have curved side edges that extend away from each other and then back toward each other moving in a toward the distal end of the ventricular anchor such that the width of the second section in the circumferential direction varies along the length of the second section.

9. The prosthetic valve of claim 8, wherein each of the second sections has an opening located between the side edges.

10. The prosthetic valve of claim 9, wherein the opening has a tear-drop shape.

11. The prosthetic device of claim 1, wherein the second sections of the distal end portions curve toward the atrial end and back toward the ventricular end starting at the first sections and moving toward the distal ends of the second sections.

12. The prosthetic device of claim 1, wherein the atrial cap comprises a plurality of atrial anchors, each comprising a proximal end portion connected to the atrial end, an intermediate portion that extends away from the ventricular end and then curves back toward the ventricular end, and a distal end portion that curves away from the intermediate portion.

13. The prosthetic device of claim 1, wherein the ventricular anchors have varying lengths and/or the atrial anchors have varying lengths.

14. The prosthetic valve of claim 1, wherein there are twelve ventricular anchors.

15. A method of implanting a prosthetic heart valve at a native atrioventricular valve region having a native valve annulus and a plurality of native leaflets, comprising:
   delivering a prosthetic heart valve to a native valve region, the prosthetic heart valve contained within an interior of a sheath of a delivery apparatus, the prosthetic heart valve comprising an annular main body, an atrial portion extending from the main body, and a plurality of ventricular anchors extending from the main body, the ventricular anchors being connected to the main body independently of each other without frame segments interconnecting adjacent anchors; and
   deploying the prosthetic heart valve from the sheath such that main body expands within the native annulus, the atrial portion is deployed in an atrium adjacent the native annulus, and the plurality of ventricular anchors extend behind the native leaflets, each ventricular anchor having a proximal end portion extending in a direction away from the atrial end, an intermediate portion extending back toward the atrial end, and a distal end portion extending toward the atrial end and radially away from the main body
   wherein the main body is a double-body structure comprising an annular inner frame portion and an annular outer frame portion overlapping the inner frame portion, the ventricular anchors extending from one of the inner and outer frame portions and the atrial portion extending from the other of the inner and outer frame portions, the outer frame portion being more flexible than the inner frame portion.

16. The method of claim 15, wherein the native valve annulus is the mitral valve annulus and the prosthetic heart valve is delivered to the annulus via the left atrium.

17. The method of claim 15, wherein a distal end portion of one or more of the plurality of ventricular anchors projects upward to contact a ventricular surface of the native valve annulus.

18. The method of claim 15, further comprising wrapping one or more of the ventricular anchors behind the native leaflets.

19. The method of claim 15, wherein deployment of the main body causes the distal end portions of the ventricular anchors to pivot inward toward the main body.

20. The method of claim 15, wherein following deployment, the prosthetic heart valve and the native valve annulus move in a generally synchronous manner during cardiac cycling.

21. The method of claim 15, wherein the atrial portion comprises an atrial sealing cap, which after being deployed, blocks the flow of blood between the native leaflets and the outside of the main body.

22. The method of claim 15, further comprising advancing the outer sheath distally to recapture the plurality of ventricular anchors within an interior of the outer sheath.

23. The method of claim 15, wherein the ventricular anchors extend from the inner frame portion.

24. The method of claim 15, wherein the inner frame portion and the outer frame portion are connected to each other with sutures.

* * * * *